United States Patent
Sadek et al.

(10) Patent No.: US 11,950,933 B1
(45) Date of Patent: Apr. 9, 2024

(54) ROBUST HEART-RATE DETECTION TECHNIQUES FOR WEARABLE HEART-RATE SENSORS

(71) Applicant: SAS Institute Inc., Cary, NC (US)

(72) Inventors: Carol Wagih Sadek, Washington, DC (US); Yuwei Liao, Cary, NC (US); Arin Chaudhuri, Raleigh, NC (US)

(73) Assignee: SAS INSTITUTE INC., Cary, NC (US)

( * ) Notice: Subject to any disclaimer, the term of this patent is extended or adjusted under 35 U.S.C. 154(b) by 0 days.

(21) Appl. No.: 18/527,070

(22) Filed: Dec. 1, 2023

Related U.S. Application Data

(60) Provisional application No. 63/527,533, filed on Jul. 18, 2023.

(51) Int. Cl.
*A61B 5/00* (2006.01)
*A61B 5/024* (2006.01)
(Continued)

(52) U.S. Cl.
CPC .......... *A61B 5/7207* (2013.01); *A61B 5/0006* (2013.01); *A61B 5/02438* (2013.01); *A61B 5/725* (2013.01); *A61B 5/726* (2013.01); *G16H 40/67* (2018.01); *G16H 50/70* (2018.01); *A61B 5/0004* (2013.01); *A61B 5/0022* (2013.01)

(58) Field of Classification Search
CPC ...... G16H 40/67; G16H 50/70; A61B 5/0004; A61B 5/02438; A61B 5/7207; A61B 5/725; A61B 5/726; A61B 5/0022
See application file for complete search history.

(56) References Cited

U.S. PATENT DOCUMENTS

2017/0086752 A1* 3/2017 Baxi ............... A61B 5/316

OTHER PUBLICATIONS

Bhardwaj et al., "A Holistic Overview of Artificial Intelligence in Detection, Classification and Prediction of Atrial Fibrillation Using Electrocardiogram: A Systematic Review and Meta-analysis," Archives of Computational Methods in Eng (2023) 30:4063-4079 https://doi.org/10.1007/s11831-023-09935-8 (Year: 2023).*

(Continued)

*Primary Examiner* — Jonathon A. Szumny
(74) *Attorney, Agent, or Firm* — Kilpatrick Townsend & Stockton LLP

(57) ABSTRACT

A heart-rate detection system can receive heartbeat data generated by a wearable heart-rate sensor worn by a wearer. The system can then execute a noise-reduction process for reducing noise in the heartbeat data. The noise-reduction process can involve applying a lowpass filter to the heartbeat data, generating wavelet coefficients by applying a wavelet transform to the filtered heartbeat data, and generating a reduced set of wavelet coefficients by thresholding the wavelet coefficients. An inverse wavelet signal can then be generated by applying an inverse wavelet transform to the reduced set of wavelet coefficients. R-peaks can be identified by performing peak detection on the instantaneous amplitudes of the data points in the inverse wavelet signal. A heart rate curve can then be generated based on the R-peaks and modified by applying a Hampel filter. Heartbeat data can then be generated based on the modified heart rate curve for output.

30 Claims, 23 Drawing Sheets

(51) Int. Cl.
  *G16H 40/67* (2018.01)
  *G16H 50/70* (2018.01)

(56) References Cited

OTHER PUBLICATIONS

Peng et al., "Electrocardiogram Signal Denoising Based on Multi-Threshold Stationary Wavelet Transform," 2022 IEEE International Symposium on Medical Measurements and Applications (MeMeA) | 978-1-6654-8299-8/22/$31.00 © 2022 IEEE | DOI: 10.1109/MEMEA54994.2022.9856544. (Year: 2022).*

Rosu et al., "Methods for Denoising the ECG Signal in Wearable Systems," ECAI 2015—International Conference—7th Edition Electronics, Computers and Artificial Intelligence; Jun. 25-Jun. 27, 2015, Bucharest, România. (Year: 2015).*

Gupta et al., "Performance Evaluation of Various Pre-Processing Techniques for R-Peak Detection in ECG Signal," IETE Journal of Research 2022, vol. 68, No. 5, 3267-3282; https://doi.org/10.1080/03772063.2020.1756473 (Year: 2022).*

Babusiak et al., "Two-Electrode ECG for Ambulatory Monitoring with Minimal Hardware Complexity," Sensors 2020, 20, 2386; doi: 10.3390/s20082386. (Year: 2020).*

Sawant et al., "Wavelet Based ECG SIgnal De-noising," 2014 First International Conference on Networks & Soft Computing. (Year: 2014).*

\* cited by examiner

ROBUST HEART-RATE DETECTION TECHNIQUES FOR WEARABLE HEART-RATE SENSORS

REFERENCE TO RELATED APPLICATION

This claims the benefit of priority under 35 U.S.C. § 119(e) to U.S. Provisional Patent Application No. 63/527,533 filed Jul. 18, 2023, the entirety of which is hereby incorporated by reference herein.

TECHNICAL FIELD

The present disclosure relates generally to wearable heart-rate sensors. More specifically, but not by way of limitation, this disclosure relates to robust heart-rate detection techniques for wearable heart-rate sensors.

BACKGROUND

Wearable heart-rate sensors, such as wearable electrocardiogram (ECG) devices, have recently become more prevalent in the digital health monitoring and among athletes. Such devices allow the wearer or other individuals to monitor the heart rate of the wearer and may issue alerts upon detecting certain heart-rate conditions. Examples of such wearable heart-rate sensors can include chest bands and smart watches. Wearable heart-rate sensors differ from standard 12-lead electrode systems, in that wearable heart-rate sensors normally have fewer electrodes (e.g., 2-4 electrodes) than 12-lead electrode systems. Wearable heart-rate sensors also normally have electrodes that are all configured to be positioned against (but not stuck with adhesive to) the same body part of the wearer, such as the wearer's chest, wrist, arm, or ankle, as opposed to being stuck with adhesive to numerous body parts of the wearer, as in a 12-lead electrode system. Additionally, wearable heart-rate sensors normally house their electrodes, wiring, and attendant electronics in a single device. In contrast, a 12-lead electrode system has twelve separate and independently placeable electrode pads that are stuck with adhesive to numerous locations on the wearer's body, with attendant cables that are freely accessible and run to an external ECG machine.

SUMMARY

One example of the present disclosure includes a system comprising one or more processors and one or more memories. The one or more memories can include program code that is executable by the one or more processors to perform operations. The operations can include receiving heartbeat data generated by a wearable heart-rate sensor worn by a wearer. The operations can also include executing a noise-reduction process for reducing noise in the heartbeat data. The noise-reduction process can involve generating a set of filtered heartbeat data by applying a lowpass filter with a cutoff frequency to the heartbeat data. The noise-reduction process can also involve generating a set of wavelet coefficients by applying a wavelet transform to the set of filtered heartbeat data. The noise-reduction process can also involve generating a reduced set of wavelet coefficients by applying a threshold to the set of wavelet coefficients, the threshold being configured to reduce noise and motion artifacts represented in the set of wavelet coefficients. The noise-reduction process can also involve generating an inverse wavelet signal by applying an inverse wavelet transform to the reduced set of wavelet coefficients, wherein each heartbeat in the heartbeat data is represented in the inverse wavelet signal by a P wave, a T wave, and an R wave. The noise-reduction process can also involve determining instantaneous amplitudes of data points in the inverse wavelet signal, the instantaneous amplitudes being determined using a Hilbert transform. The noise-reduction process can also involve identifying a set of R-peaks by performing peak detection on the instantaneous amplitudes. The noise-reduction process can also involve generating a heart rate curve based on the set of R-peaks. The noise-reduction process can also involve generating a modified heart rate curve by applying a Hampel filter to the heart rate curve. The operations can further involve determining heart rate data based on the modified heart rate curve, and outputting the heart rate data associated with the wearer.

Another example of the present disclosure includes a non-transitory computer-readable medium comprising program code that is executable by one or more processors for causing the one or more processors to perform operations. The operations can include receiving heartbeat data generated by a wearable heart-rate sensor worn by a wearer. The operations can also include executing a noise-reduction process for reducing noise in the heartbeat data. The noise-reduction process can involve generating a set of filtered heartbeat data by applying a lowpass filter with a cutoff frequency to the heartbeat data. The noise-reduction process can also involve generating a set of wavelet coefficients by applying a wavelet transform to the set of filtered heartbeat data. The noise-reduction process can also involve generating a reduced set of wavelet coefficients by applying a threshold to the set of wavelet coefficients, the threshold being configured to reduce noise and motion artifacts represented in the set of wavelet coefficients. The noise-reduction process can also involve generating an inverse wavelet signal by applying an inverse wavelet transform to the reduced set of wavelet coefficients, wherein each heartbeat in the heartbeat data is represented in the inverse wavelet signal by a P wave, a T wave, and an R wave. The noise-reduction process can also involve determining instantaneous amplitudes of data points in the inverse wavelet signal, the instantaneous amplitudes being determined using a Hilbert transform. The noise-reduction process can also involve identifying a set of R-peaks by performing peak detection on the instantaneous amplitudes. The noise-reduction process can also involve generating a heart rate curve based on the set of R-peaks. The noise-reduction process can also involve generating a modified heart rate curve by applying a Hampel filter to the heart rate curve. The operations can further involve determining heart rate data based on the modified heart rate curve, and outputting the heart rate data associated with the wearer.

Still another example of the present disclosure includes a method of operations that can be implemented by one or more processors. The operations can include receiving heartbeat data generated by a wearable heart-rate sensor worn by a wearer. The operations can also include executing a noise-reduction process for reducing noise in the heartbeat data. The noise-reduction process can involve generating a set of filtered heartbeat data by applying a lowpass filter with a cutoff frequency to the heartbeat data. The noise-reduction process can also involve generating a set of wavelet coefficients by applying a wavelet transform to the set of filtered heartbeat data. The noise-reduction process can also involve generating a reduced set of wavelet coefficients by applying a threshold to the set of wavelet coefficients, the threshold being configured to reduce noise and motion artifacts represented in the set of wavelet coefficients. The noise-reduction process can also involve generating an inverse wavelet signal by applying an inverse wavelet transform to the reduced set of wavelet coefficients, wherein each heartbeat in the heartbeat data is represented in the inverse wavelet signal by a P wave, a T wave, and an R wave. The noise-reduction process can also involve determining instantaneous amplitudes of data points in the inverse wavelet signal, the instantaneous amplitudes being determined using a Hilbert transform. The noise-reduction process can also involve identifying a set of R-peaks by performing peak detection on the instantaneous amplitudes. The noise-reduction process can also involve generating a heart rate curve based on the set of R-peaks. The noise-reduction process can also involve generating a modified heart rate curve by applying a Hampel filter to the heart rate curve. The operations can further involve determining heart rate data based on the modified heart rate curve, and outputting the heart rate data associated with the wearer.

This summary is not intended to identify key or essential features of the claimed subject matter, nor is it intended to be used in isolation to determine the scope of the claimed subject matter. The subject matter should be understood by reference to appropriate portions of the entire specification, any or all drawings, and each claim.

The foregoing, together with other features and examples, will become more apparent upon referring to the following specification, claims, and accompanying drawings.

BRIEF DESCRIPTION OF THE DRAWINGS

The present disclosure is described in conjunction with the appended figures.

Figure 1:
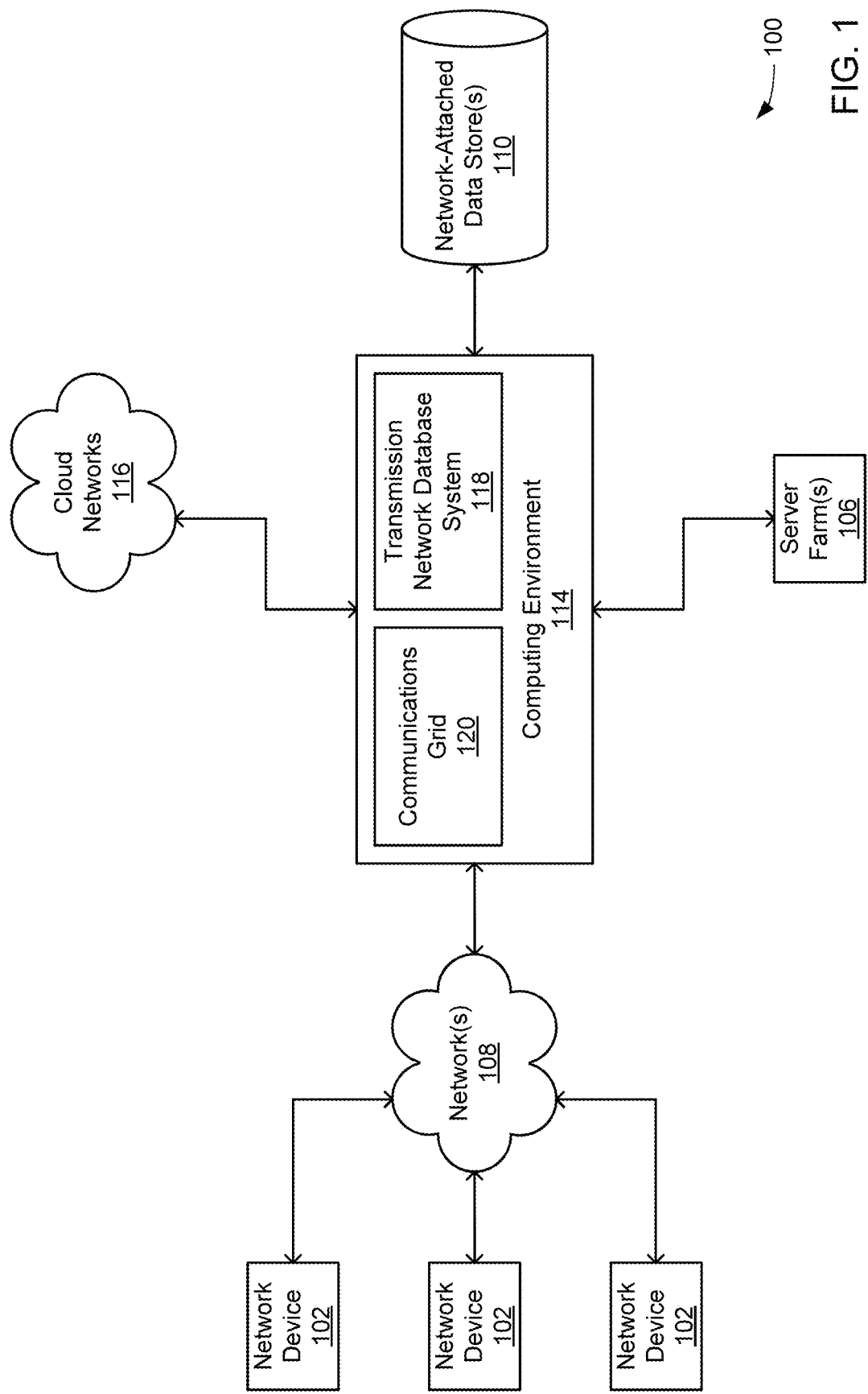
FIG. 1 shows an example of the hardware components of a data transmission network according to some aspects of the present disclosure.

In the appended figures, similar components or features can have the same reference number. Further, various components of the same type may be distinguished by following the reference number with a lowercase letter that distinguishes among the similar components. If only the first reference number is used in the specification, the description is applicable to any one of the similar components having the same first reference number irrespective of the lowercase letter.

DETAILED DESCRIPTION

One common type of heart-rate sensor is a wearable heart-rate sensor, such as a wearable ECG device. Such wearable heart-rate sensors have recently grown in popularity. These "wearable heart-rate sensors" are wearable devices with one or more electrodes designed to be positioned against the skin of a wearer for use in detecting the heart rate of the wearer. Such wearable heart-rate sensors may have straps or other mechanisms that wrap around a body part of the wearer to position the electrodes against the wearer's skin. The electrodes may or may not be adhered to the skin of the wearer with an adhesive such as tape or glue. When the electrodes are not adhered to the user's body, this lack of adhesion can allow the wearable heart-rate sensor to slide against the wearer's skin, particularly when the wearer is engaged in physical activity such as exercise. The electrodes, their wires, and any attendant electronics may be disposed in or on the housing of the wearable device. Such wearable heart-rate sensors are generally considered to be different from other types of heart-rate sensors, such as a standard 12-lead electrode system, in which the electrodes are adhered to the wearer's body (to prevent them from sliding against the skin of the wearer) and have exposed wiring, despite those electrodes also technically being "worn" by the user.

Wearable heart-rate sensors can produce higher levels of noise than other kinds of heart-rate sensors, such as standard 12-lead electrode systems, because unadhered electrodes can slide against the skin of the wearer when the wearer is in motion. Analyzing signals from wearable heart-rate sensors can be challenging because of the high levels of noise and the presence of motion artifacts, which are less prevalent in ECG systems in which the electrodes are adhered to the wearer's body, such as a 12-lead electrode system. Because of the movement of the electrodes against the skin, motion artifacts are common when a subject performs any physical activity while wearing a wearable heart-rate sensor. ECG signals from wearable heart-rate sensors also tend to have high levels of noise dispersed along the entire signal when the subject is in motion, rather than occurring in small, isolated locations along the signal. And because of the higher level of noise dispersed throughout the signal during physical activity, sweat and changes in electrolytes can lead to false detection of R-peaks in the QRS complexes of the ECG signal, which can result in erroneous heart-rate measurements. As used herein, a QRS complex is a combination of a Q wave, R wave, and S wave that can represent the ventricular depolarization of the heart. The R-peaks are the peaks of the R waves in the QRS complexes of the ECG signal.

Some examples of the present disclosure can overcome one or more of the abovementioned problems by providing robust signal-processing techniques for detecting the heart rate of a wearer using a wearable heart-rate sensor. The signal-processing techniques can be used both when the wearer is stationary and when the wearer is in motion. The improved signal-processing techniques can remove (e.g., filter) noise from an ECG signal using a unique combination of lowpass digital filtering, stationary wavelet transform, instantaneous amplitude, peak-finding methods, and Hampel filtering to provide accurate measurements of a wearer's heart rate. The techniques are not dependent on the wearer and do not require any prior knowledge of the wearer, do not require any training of models, and provide accurate results. Even when a subject is in motion and the ECG signal includes motion artifacts, the techniques described herein can still locate R-peaks in the QRS complex of the ECG signal with relatively high accuracy, allowing for accurate heart-rate measurements.

As one particular example, a user can wear a wearable device, such as a smart watch. The wearable device may include a display and electrodes. When worn by the user, the wearable device can position the electrodes against the user's skin, without the electrodes being adhered to the user's skin. The wearable device can receive heartbeat data generated using the electrodes. The heartbeat data may be an ECG signal that may contain motion artifacts and other noise, particularly if the user is in motion while wearing the wearable device due to the sliding of the electrodes against the wearer's skin and/or other factors. To help improve the quality of and reduce the noise in the ECG signal, the wearable device can implement a noise-reduction process on the heartbeat data. In some examples, the noise-reduction process can involve generating a filtered ECG signal by applying a lowpass filter with a cutoff frequency to the ECG signal. A set of wavelet coefficients can then be generated by applying a wavelet transform, such as a stationary wavelet transform, to the filtered ECG signal. A threshold can then be applied to the set of wavelet coefficients to produce a reduced set of wavelet coefficients. The threshold can be selected to reduce noise and motion artifacts represented in the set of wavelet coefficients. An inverse wavelet transform can then be applied to the reduced set of wavelet coefficients, which can yield an inverse wavelet signal. Each heartbeat can be represented in the inverse wavelet signal by a P-wave, a T-wave, and an R-wave. The inverse wavelet signal can then be transformed using a Hilbert transform to determine instantaneous amplitudes of data points in the inverse wavelet signal. Peak detection can be performed on the instantaneous amplitudes to identify a set of R-peaks. From the set of R-peaks, a heart rate curve can be generated that indicates the heart rate of the wearer over time. The heart rates in the heart rate curve can be generated based on the distances between successive R-peaks in the set of R-peaks. The heart rate curve can then be modified (e.g., smoothed) by applying a Hampel filter to the heart rate curve. The wearable device can then output the heart rate curve, or an individual heart rate therefrom, associated with the wearer on the display.

These illustrative examples are given to introduce the reader to the general subject matter discussed here and are not intended to limit the scope of the disclosed concepts. The following sections describe various additional features and examples with reference to the drawings in which like numerals indicate like elements but, like the illustrative examples, should not be used to limit the present disclosure.

FIG. 1 is a block diagram that provides an illustration of the hardware components of a data transmission network 100, according to embodiments of the present technology. Data transmission network 100 is a specialized computer system that may be used for processing large amounts of data where a large number of computer processing cycles are required.

Data transmission network 100 may also include computing environment 114. Computing environment 114 may be a specialized computer or other machine that processes the data received within the data transmission network 100. Data transmission network 100 also includes one or more network devices 102. Network devices 102 may include client devices that attempt to communicate with computing environment 114. For example, network devices 102 may send data to the computing environment 114 to be processed, may send signals to the computing environment 114 to control different aspects of the computing environment or the data it is processing, among other reasons. Network devices 102 may interact with the computing environment 114 through a number of ways, such as, for example, over one or more networks 108. As shown in FIG. 1, computing environment 114 may include one or more other systems. For example, computing environment 114 may include a database system 118 and/or a communications grid 120.

Figure 8:
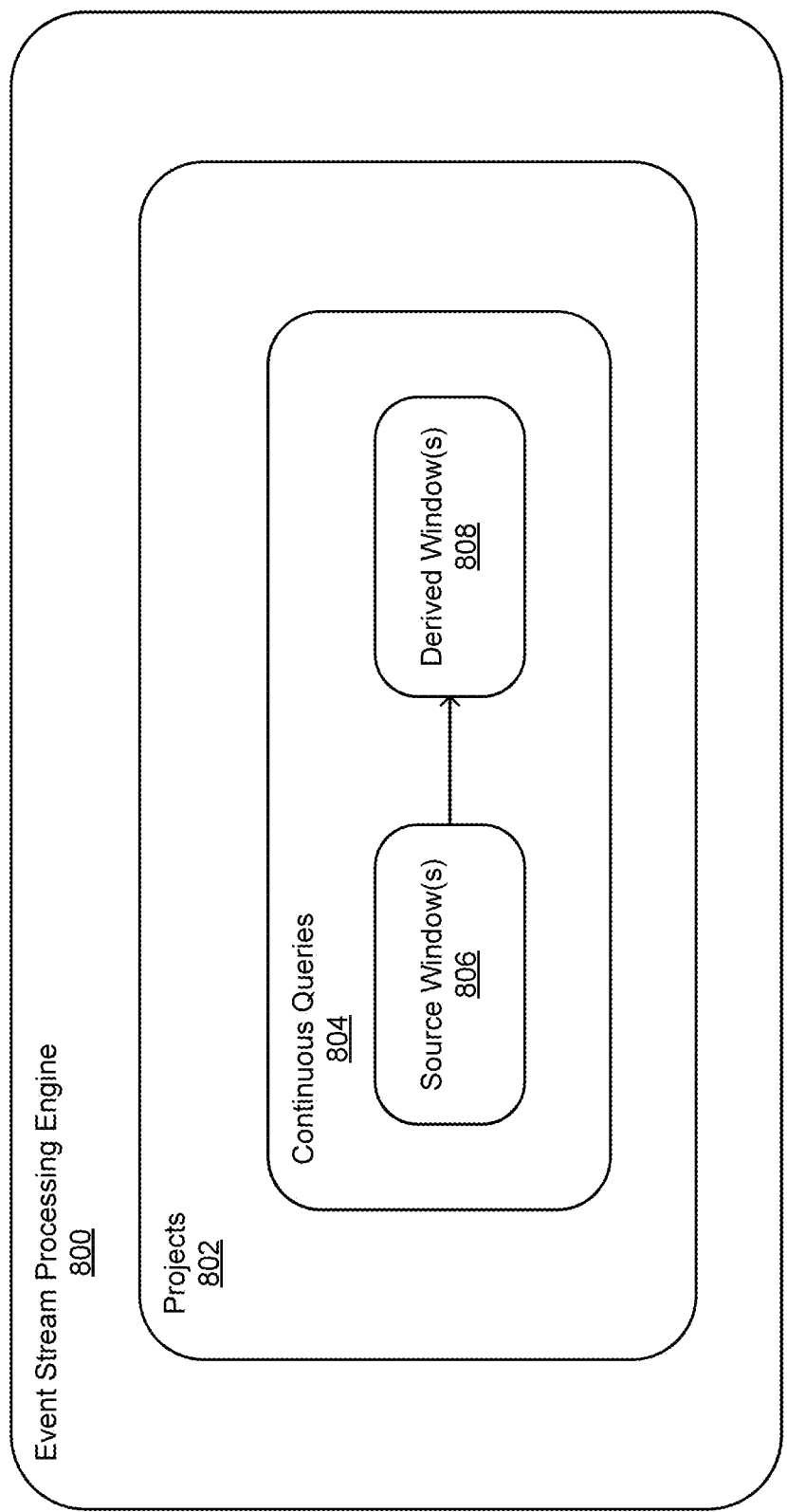
FIG. 8 shows a block diagram including components of an Event Stream Processing Engine (ESPE) according to some aspects of the present disclosure.
Figure 9:
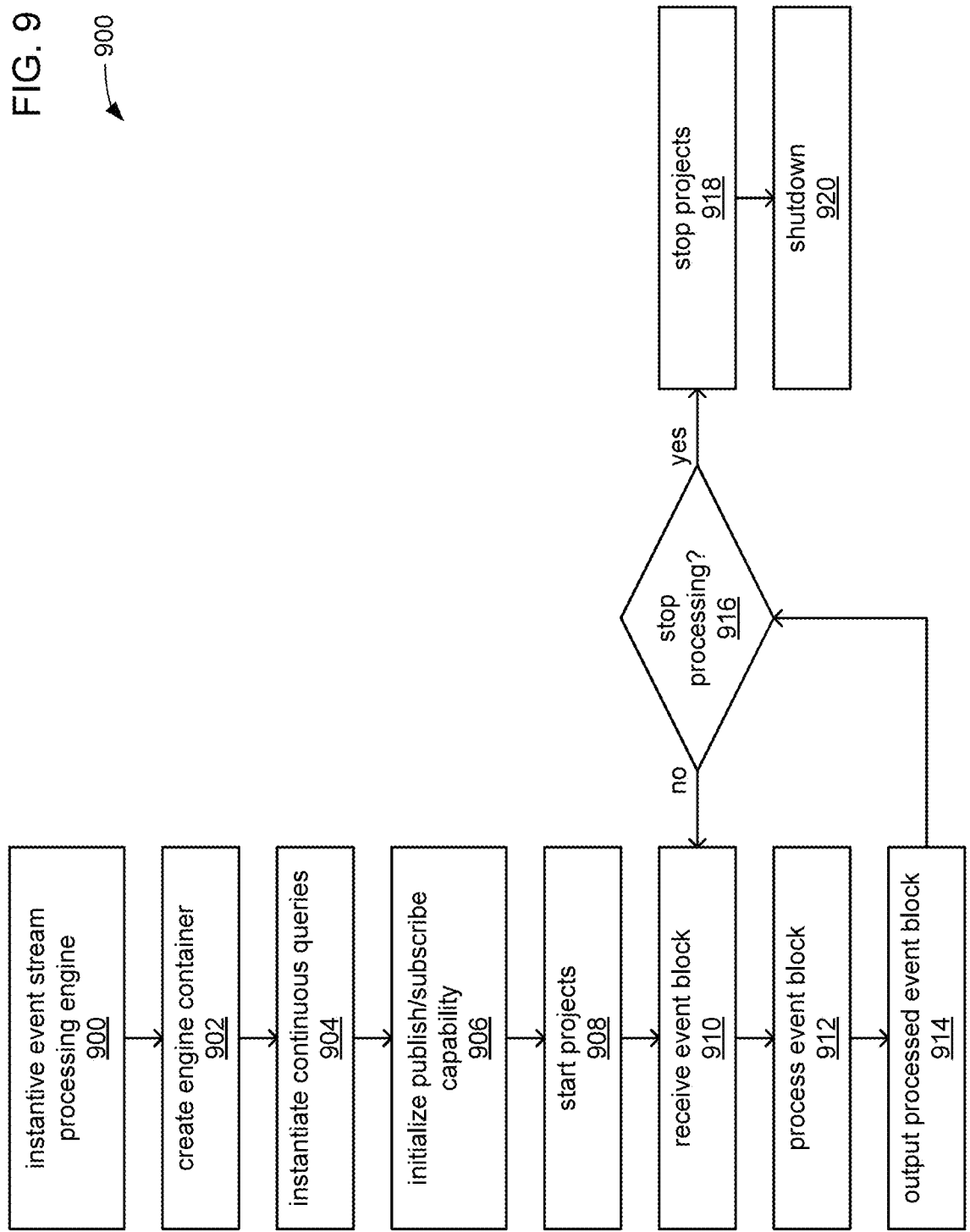
FIG. 9 shows a flow chart of an example process including operations performed by an event stream processing engine according to some aspects of the present disclosure.
Figure 10:
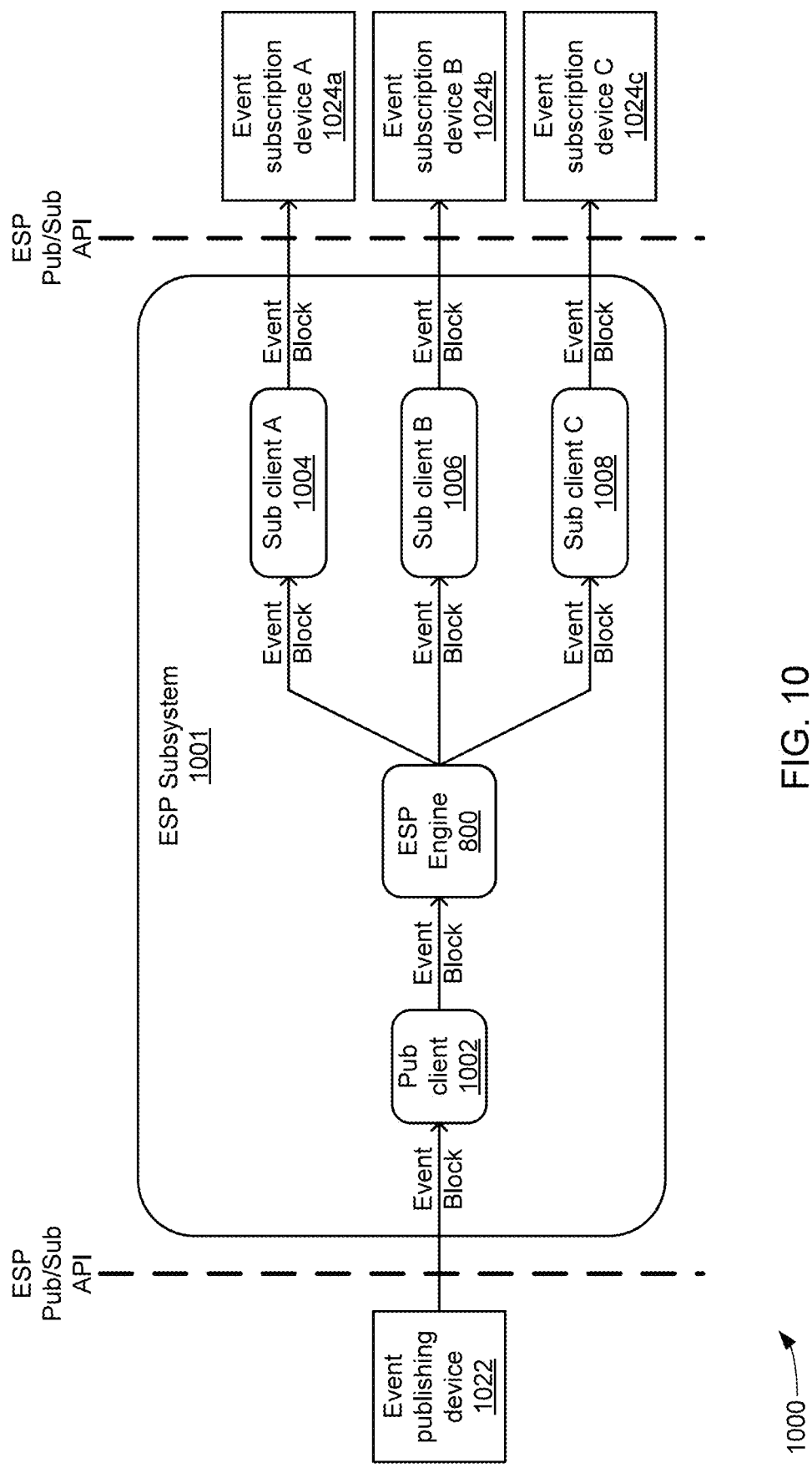
FIG. 10 shows an ESP system interfacing between publishing device and event subscribing devices according to some aspects of the present disclosure.

In other embodiments, network devices 102 may provide a large amount of data, either all at once or streaming over a period of time (e.g., using event stream processing (ESP), described further with respect to FIGS. 8-10), to the computing environment 114 via networks 108. For example, network devices 102 may include network computers, sensors, databases, or other devices that may transmit or otherwise provide data to computing environment 114. For example, network devices 102 may include local area network devices, such as routers, hubs, switches, or other computer networking devices. These devices may provide a variety of stored or generated data, such as network data or data specific to the network devices themselves. Network devices 102 may also include sensors that monitor their environment or other devices to collect data regarding that environment or those devices, and such network devices may provide data they collect over time. Network devices 102 may also include devices within the internet of things, such as devices within a home automation network. Some of these devices may be referred to as edge devices, and may involve edge computing circuitry. Data may be transmitted by network devices 102 directly to computing environment 114 or to network-attached data stores, such as network-attached data stores 110 for storage so that the data may be retrieved later by the computing environment 114 or other portions of data transmission network 100.

Data transmission network 100 may also include one or more network-attached data stores 110. Network-attached data stores 110 are used to store data to be processed by the computing environment 114 as well as any intermediate or final data generated by the computing system in non-volatile memory. However, in certain embodiments, the configuration of the computing environment 114 allows its operations to be performed such that intermediate and final data results can be stored solely in volatile memory (e.g., RAM), without a requirement that intermediate or final data results be stored to non-volatile types of memory (e.g., disk). This can be useful in certain situations, such as when the computing environment 114 receives ad hoc queries from a user and when responses, which are generated by processing large amounts of data, need to be generated on-the-fly. In this non-limiting situation, the computing environment 114 may be configured to retain the processed information within memory so that responses can be generated for the user at different levels of detail as well as allow a user to interactively query against this information.

Network-attached data stores 110 may store a variety of different types of data organized in a variety of different ways and from a variety of different sources. For example, network-attached data storage may include storage other than primary storage located within computing environment 114 that is directly accessible by processors located therein. Network-attached data storage may include secondary, tertiary or auxiliary storage, such as large hard drives, servers, virtual memory, among other types. Storage devices may include portable or non-portable storage devices, optical storage devices, and various other mediums capable of storing or containing data. A machine-readable storage medium or computer-readable storage medium may include a non-transitory medium in which data can be stored and that does not include carrier waves and/or transitory electronic signals. Examples of a non-transitory medium may include, for example, a magnetic disk or tape, optical storage media such as compact disk or digital versatile disk, flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, and network transmission, among others. Furthermore, the data stores may hold a variety of different types of data. For example, network-attached data stores 110 may hold unstructured (e.g., raw) data, such as manufacturing data (e.g., a database containing records identifying products being manufactured with parameter data for each product, such as colors and models) or product sales databases (e.g., a database containing individual data records identifying details of individual product sales).

The unstructured data may be presented to the computing environment 114 in different forms such as a flat file or a conglomerate of data records, and may have data values and accompanying time stamps. The computing environment 114 may be used to analyze the unstructured data in a variety of ways to determine the best way to structure (e.g., hierarchically) that data, such that the structured data is tailored to a type of further analysis that a user wishes to perform on the data. For example, after being processed, the unstructured time stamped data may be aggregated by time (e.g., into daily time period units) to generate time series data and/or structured hierarchically according to one or more dimensions (e.g., parameters, attributes, and/or variables). For example, data may be stored in a hierarchical data structure, such as a ROLAP OR MOLAP database, or may be stored in another tabular form, such as in a flat-hierarchy form.

Data transmission network 100 may also include one or more server farms 106. Computing environment 114 may route select communications or data to the one or more server farms 106 or one or more servers within the server farms. Server farms 106 can be configured to provide information in a predetermined manner. For example, server farms 106 may access data to transmit in response to a communication. Server farms 106 may be separately housed from each other device within data transmission network 100, such as computing environment 114, and/or may be part of a device or system.

Server farms 106 may host a variety of different types of data processing as part of data transmission network 100. Server farms 106 may receive a variety of different data from network devices 102, from computing environment 114, from cloud network 116, or from other sources. The data may have been obtained or collected from one or more sensors, as inputs from a control database, or may have been received as inputs from an external system or device. Server farms 106 may assist in processing the data by turning raw data into processed data based on one or more rules implemented by the server farms. For example, sensor data may be analyzed to determine changes in an environment over time or in real-time.

Data transmission network 100 may also include one or more cloud networks 116. Cloud network 116 may include a cloud infrastructure system that provides cloud services. In certain embodiments, services provided by the cloud network 116 may include a host of services that are made available to users of the cloud infrastructure system on demand. Cloud network 116 is shown in FIG. 1 as being connected to computing environment 114 (and therefore having computing environment 114 as its client or user), but cloud network 116 may be connected to or utilized by any of the devices in FIG. 1. Services provided by the cloud network can dynamically scale to meet the needs of its users. The cloud network 116 may include one or more computers, servers, and/or systems. In some embodiments, the computers, servers, and/or systems that make up the cloud network 116 are different from the user's own on-premises computers, servers, and/or systems. For example, the cloud network 116 may host an application, and a user may, via a communication network such as the Internet, on demand, order and use the application.

While each device, server and system in FIG. 1 is shown as a single device, it will be appreciated that multiple devices may instead be used. For example, a set of network devices can be used to transmit various communications from a single user, or remote server may include a server stack. As another example, data may be processed as part of computing environment 114.

Each communication within data transmission network 100 (e.g., between client devices, between servers 106 and computing environment 114 or between a server and a device) may occur over one or more networks 108. Networks 108 may include one or more of a variety of different types of networks, including a wireless network, a wired network, or a combination of a wired and wireless network. Examples of suitable networks include the Internet, a personal area network, a local area network (LAN), a wide area network (WAN), or a wireless local area network (WLAN). A wireless network may include a wireless interface or combination of wireless interfaces. As an example, a network in the one or more networks 108 may include a short-range communication channel, such as a BLUETOOTH® communication channel or a BLUETOOTH® Low Energy communication channel. A wired network may include a wired interface. The wired and/or wireless networks may be implemented using routers, access points, bridges, gateways, or the like, to connect devices in the network 108, as will be further described with respect to FIG. 2. The one or more networks 108 can be incorporated entirely within or can include an intranet, an extranet, or a combination thereof. In one embodiment, communications between two or more systems and/or devices can be achieved by a secure communications protocol, such as secure sockets layer (SSL) or transport layer security (TLS). In addition, data and/or transactional details may be encrypted.

Some aspects may utilize the Internet of Things (IoT), where things (e.g., machines, devices, phones, sensors) can be connected to networks and the data from these things can be collected and processed within the things and/or external to the things. For example, the IoT can include sensors in many different devices, and high value analytics can be applied to identify hidden relationships and drive increased efficiencies. This can apply to both big data analytics and real-time (e.g., ESP) analytics. This will be described further below with respect to FIG. 2.

As noted, computing environment 114 may include a communications grid 120 and a transmission network database system 118. Communications grid 120 may be a grid-based computing system for processing large amounts of data. The transmission network database system 118 may be for managing, storing, and retrieving large amounts of data that are distributed to and stored in the one or more network-attached data stores 110 or other data stores that reside at different locations within the transmission network database system 118. The compute nodes in the grid-based computing system 120 and the transmission network database system 118 may share the same processor hardware, such as processors that are located within computing environment 114.

Figure 2:
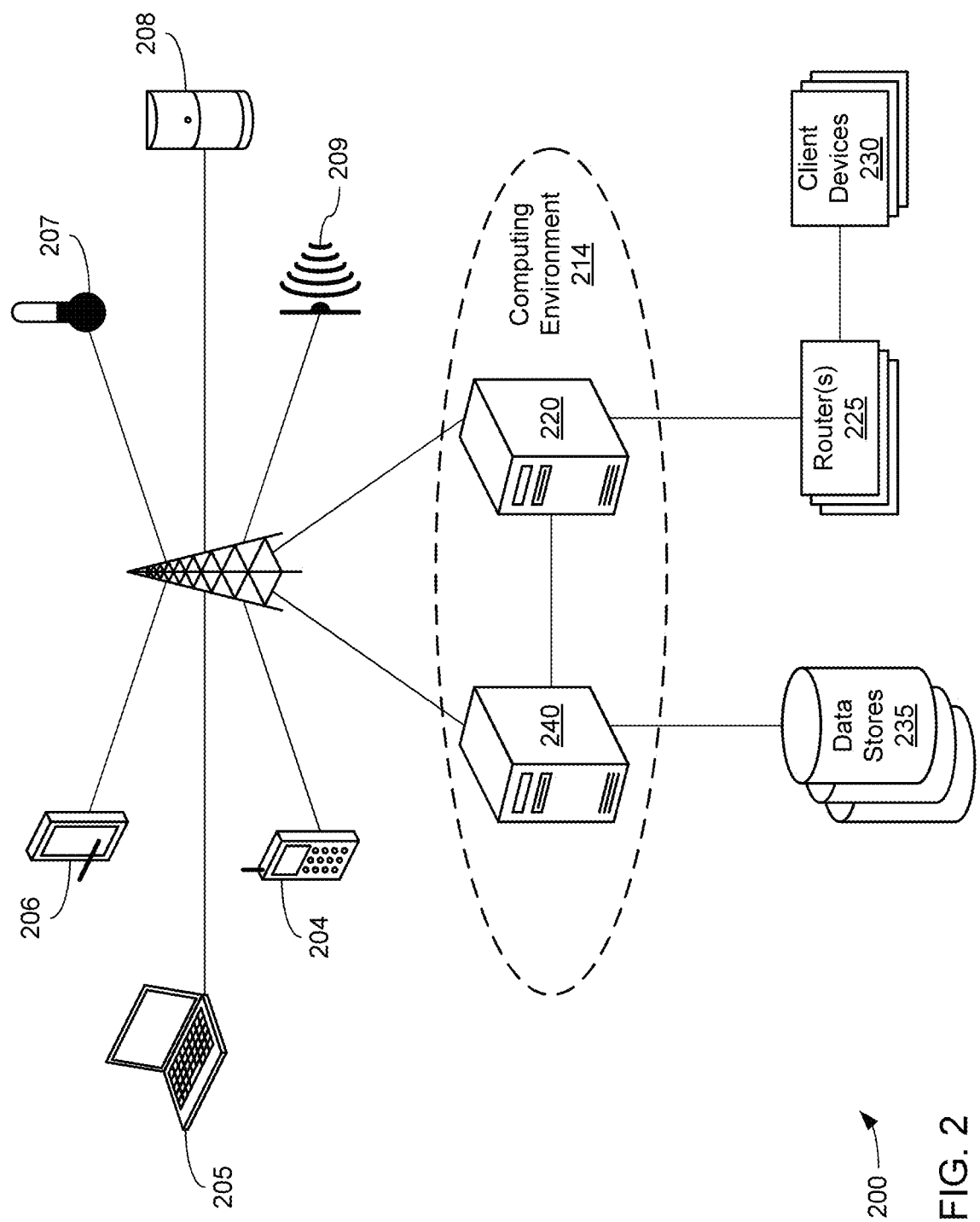
FIG. 2 shows an example network including an example set of devices communicating with each other over an exchange system according to some aspects of the present disclosure.

FIG. 2 illustrates an example network including an example set of devices communicating with each other over an exchange system and via a network, according to embodiments of the present technology. As noted, each communication within data transmission network 100 may occur over one or more networks. System 200 includes a network device 204 configured to communicate with a variety of types of client devices, for example client devices 230, over a variety of types of communication channels.

As shown in FIG. 2, network device 204 can transmit a communication over a network (e.g., a cellular network via a base station). The communication can be routed to another network device, such as network devices 205-209, via base station. The communication can also be routed to computing environment 214 via base station. For example, network device 204 may collect data either from its surrounding environment or from other network devices (such as network devices 205-209) and transmit that data to computing environment 214.

Although network devices 204-209 are shown in FIG. 2 as a mobile phone, laptop computer, tablet computer, temperature sensor, motion sensor, and audio sensor respectively, the network devices may be or include sensors that are sensitive to detecting characteristics of their environment. For example, the network devices may include sensors such as water sensors, power sensors, electrical current sensors, chemical sensors, optical sensors, pressure sensors, geographic or position sensors (e.g., GPS), velocity sensors, acceleration sensors, flow rate sensors, among others. Examples of characteristics that may be sensed include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, and electrical current, among others. The sensors may be mounted to various components used as part of a variety of different types of systems (e.g., an oil drilling operation). The network devices may detect and record data related to the environment that it monitors, and transmit that data to computing environment 214.

As noted, one type of system that may include various sensors that collect data to be processed and/or transmitted to a computing environment according to certain embodiments includes an oil drilling system. For example, the one or more drilling operation sensors may include surface sensors that measure a hook load, a fluid rate, a temperature and a density in and out of the wellbore, a standpipe pressure, a surface torque, a rotation speed of a drill pipe, a rate of penetration, a mechanical specific energy, etc., and downhole sensors that measure a rotation speed of a bit, fluid densities, downhole torque, downhole vibration (axial, tangential, lateral), a weight applied at a drill bit, an annular pressure, a differential pressure, an azimuth, an inclination, a dog leg severity, a measured depth, a vertical depth, a downhole temperature, etc. Besides the raw data collected directly by the sensors, other data may include parameters either developed by the sensors or assigned to the system by a client or other controlling device. For example, one or more drilling operation control parameters may control settings such as a mud motor speed to flow ratio, a bit diameter, a predicted formation top, seismic data, weather data, etc. Other data may be generated using physical models such as an earth model, a weather model, a seismic model, a bottom hole assembly model, a well plan model, an annular friction model, etc. In addition to sensor and control settings, predicted outputs, of for example, the rate of penetration, mechanical specific energy, hook load, flow in fluid rate, flow out fluid rate, pump pressure, surface torque, rotation speed of the drill pipe, annular pressure, annular friction pressure, annular temperature, equivalent circulating density, etc. may also be stored in the data warehouse.

In another example, another type of system that may include various sensors that collect data to be processed and/or transmitted to a computing environment according to certain embodiments includes a home automation or similar automated network in a different environment, such as an office space, school, public space, sports venue, or a variety of other locations. Network devices in such an automated network may include network devices that allow a user to access, control, and/or configure various home appliances located within the user's home (e.g., a television, radio, light, fan, humidifier, sensor, microwave, iron, and/or the like), or outside of the user's home (e.g., exterior motion sensors, exterior lighting, garage door openers, sprinkler systems, or the like). For example, network device 102 may include a home automation switch that may be coupled with a home appliance. In another embodiment, a network device can allow a user to access, control, and/or configure devices, such as office-related devices (e.g., copy machine, printer, or fax machine), audio and/or video related devices (e.g., a receiver, a speaker, a projector, a DVD player, or a television), media-playback devices (e.g., a compact disc player, a CD player, or the like), computing devices (e.g., a home computer, a laptop computer, a tablet, a personal digital assistant (PDA), a computing device, or a wearable device), lighting devices (e.g., a lamp or recessed lighting), devices associated with a security system, devices associated with an alarm system, devices that can be operated in an automobile (e.g., radio devices, navigation devices), and/or the like. Data may be collected from such various sensors in raw form, or data may be processed by the sensors to create parameters or other data either developed by the sensors based on the raw data or assigned to the system by a client or other controlling device.

In another example, another type of system that may include various sensors that collect data to be processed and/or transmitted to a computing environment according to certain embodiments includes a power or energy grid. A variety of different network devices may be included in an energy grid, such as various devices within one or more power plants, energy farms (e.g., wind farm, solar farm, among others) energy storage facilities, factories, homes and businesses of consumers, among others. One or more of such devices may include one or more sensors that detect energy gain or loss, electrical input or output or loss, and a variety of other efficiencies. These sensors may collect data to inform users of how the energy grid, and individual devices within the grid, may be functioning and how they may be made more efficient.

Network device sensors may also perform processing on data they collect before transmitting the data to the computing environment 114, or before deciding whether to transmit data to the computing environment 114. For example, network devices may determine whether data collected meets certain rules, for example by comparing data or values calculated from the data and comparing that data to one or more thresholds. The network device may use this data and/or comparisons to determine if the data should be transmitted to the computing environment 214 for further use or processing.

Computing environment 214 may include machines 220 and 240. Although computing environment 214 is shown in FIG. 2 as having two machines, 220 and 240, computing environment 214 may have only one machine or may have more than two machines. The machines that make up computing environment 214 may include specialized computers, servers, or other machines that are configured to individually and/or collectively process large amounts of data. The computing environment 214 may also include storage devices that include one or more databases of structured data, such as data organized in one or more hierarchies, or unstructured data. The databases may communicate with the processing devices within computing environment 214 to distribute data to them. Since network devices may transmit data to computing environment 214, that data may be received by the computing environment 214 and subsequently stored within those storage devices. Data used by computing environment 214 may also be stored in data stores 235, which may also be a part of or connected to computing environment 214.

Computing environment 214 can communicate with various devices via one or more routers 225 or other inter-network or intra-network connection components. For example, computing environment 214 may communicate with client devices 230 via one or more routers 225. Computing environment 214 may collect, analyze and/or store data from or pertaining to communications, client device operations, client rules, and/or user-associated actions stored at one or more data stores 235. Such data may influence communication routing to the devices within computing environment 214, how data is stored or processed within computing environment 214, among other actions.

Notably, various other devices can further be used to influence communication routing and/or processing between devices within computing environment 214 and with devices outside of computing environment 214. For example, as shown in FIG. 2, computing environment 214 may include a machine 240 that is a web server. Thus, computing environment 214 can retrieve data of interest, such as client information (e.g., product information, client rules, etc.), technical product details, news, current or predicted weather, and so on.

In addition to computing environment 214 collecting data (e.g., as received from network devices, such as sensors, and client devices or other sources) to be processed as part of a big data analytics project, it may also receive data in real time as part of a streaming analytics environment. As noted, data may be collected using a variety of sources as communicated via different kinds of networks or locally. Such data may be received on a real-time streaming basis. For example, network devices may receive data periodically from network device sensors as the sensors continuously sense, monitor and track changes in their environments. Devices within computing environment 214 may also perform pre-analysis on data it receives to determine if the data received should be processed as part of an ongoing project. The data received and collected by computing environment 214, no matter what the source or method or timing of receipt, may be processed over a period of time for a client to determine results data based on the client's needs and rules.

Figure 3:
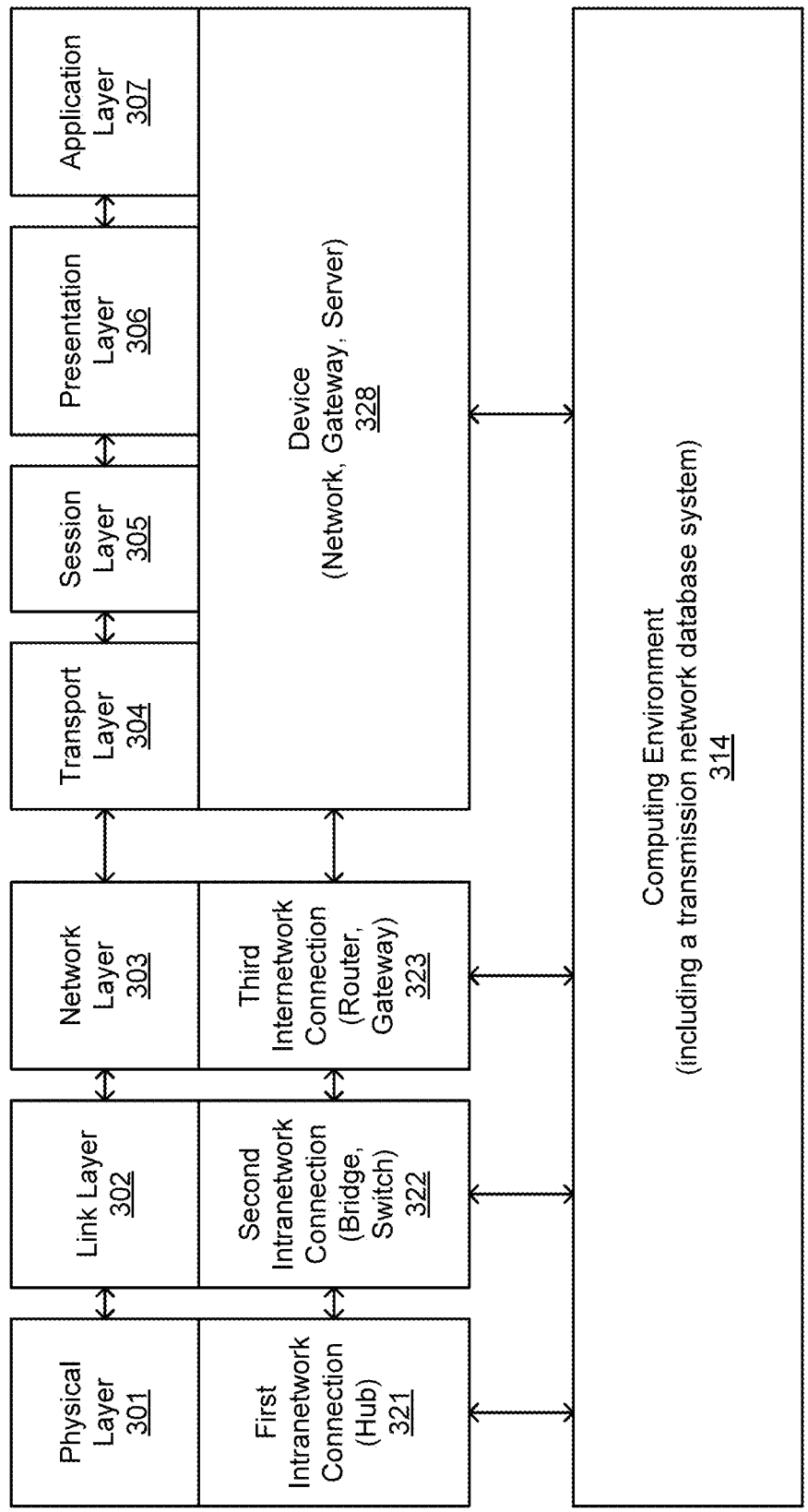
FIG. 3 shows an example representation of a conceptual model of a communications protocol system according to some aspects of the present disclosure.

FIG. 3 illustrates a representation of a conceptual model of a communications protocol system, according to embodiments of the present technology. More specifically, FIG. 3 identifies operation of a computing environment in an Open Systems Interaction model that corresponds to various connection components. The model 300 shows, for example, how a computing environment, such as computing environment 314 (or computing environment 214 in FIG. 2) may communicate with other devices in its network, and control how communications between the computing environment and other devices are executed and under what conditions.

The model can include layers 301-307. The layers are arranged in a stack. Each layer in the stack serves the layer one level higher than it (except for the application layer, which is the highest layer), and is served by the layer one level below it (except for the physical layer, which is the lowest layer). The physical layer is the lowest layer because it receives and transmits raw bites of data, and is the farthest layer from the user in a communications system. On the other hand, the application layer is the highest layer because it interacts directly with a software application.

As noted, the model includes a physical layer 301. Physical layer 301 represents physical communication, and can define parameters of that physical communication. For example, such physical communication may come in the form of electrical, optical, or electromagnetic signals. Physical layer 301 also defines protocols that may control communications within a data transmission network.

Link layer 302 defines links and mechanisms used to transmit (i.e., move) data across a network. The link layer 302 manages node-to-node communications, such as within a grid computing environment. Link layer 302 can detect and correct errors (e.g., transmission errors in the physical layer 301). Link layer 302 can also include a media access control (MAC) layer and logical link control (LLC) layer.

Network layer 303 defines the protocol for routing within a network. In other words, the network layer coordinates transferring data across nodes in a same network (e.g., such as a grid computing environment). Network layer 303 can also define the processes used to structure local addressing within the network.

Transport layer 304 can manage the transmission of data and the quality of the transmission and/or receipt of that data. Transport layer 304 can provide a protocol for transferring data, such as, for example, a Transmission Control Protocol (TCP). Transport layer 304 can assemble and disassemble data frames for transmission. The transport layer can also detect transmission errors occurring in the layers below it.

Session layer 305 can establish, maintain, and manage communication connections between devices on a network. In other words, the session layer controls the dialogues or nature of communications between network devices on the network. The session layer may also establish checkpointing, adjournment, termination, and restart procedures.

Presentation layer 306 can provide translation for communications between the application and network layers. In other words, this layer may encrypt, decrypt and/or format data based on data types and/or encodings known to be accepted by an application or network layer.

Application layer 307 interacts directly with software applications and end users, and manages communications between them. Application layer 307 can identify destinations, local resource states or availability and/or communication content or formatting using the applications.

Intra-network connection components 321 and 322 are shown to operate in lower levels, such as physical layer 301 and link layer 302, respectively. For example, a hub can operate in the physical layer, a switch can operate in the link layer, and a router can operate in the network layer. Inter-network connection components 323 and 328 are shown to operate on higher levels, such as layers 303-307. For example, routers can operate in the network layer and network devices can operate in the transport, session, presentation, and application layers.

As noted, a computing environment 314 can interact with and/or operate on, in various embodiments, one, more, all or any of the various layers. For example, computing environment 314 can interact with a hub (e.g., via the link layer) so as to adjust which devices the hub communicates with. The physical layer may be served by the link layer, so it may implement such data from the link layer. For example, the computing environment 314 may control which devices it will receive data from. For example, if the computing environment 314 knows that a certain network device has turned off, broken, or otherwise become unavailable or unreliable, the computing environment 314 may instruct the hub to prevent any data from being transmitted to the computing environment 314 from that network device. Such a process may be beneficial to avoid receiving data that is inaccurate or that has been influenced by an uncontrolled environment. As another example, computing environment 314 can communicate with a bridge, switch, router or gateway and influence which device within the system (e.g., system 200) the component selects as a destination. In some embodiments, computing environment 314 can interact with various layers by exchanging communications with equipment operating on a particular layer by routing or modifying existing communications. In another embodiment, such as in a grid computing environment, a node may determine how data within the environment should be routed (e.g., which node should receive certain data) based on certain parameters or information provided by other layers within the model.

As noted, the computing environment 314 may be a part of a communications grid environment, the communications of which may be implemented as shown in the protocol of FIG. 3. For example, referring back to FIG. 2, one or more of machines 220 and 240 may be part of a communications grid computing environment. A gridded computing environment may be employed in a distributed system with non-interactive workloads where data resides in memory on the machines, or compute nodes. In such an environment, analytic code, instead of a database management system, controls the processing performed by the nodes. Data is co-located by pre-distributing it to the grid nodes, and the analytic code on each node loads the local data into memory. Each node may be assigned a particular task such as a portion of a processing project, or to organize or control other nodes within the grid.

Figure 4:
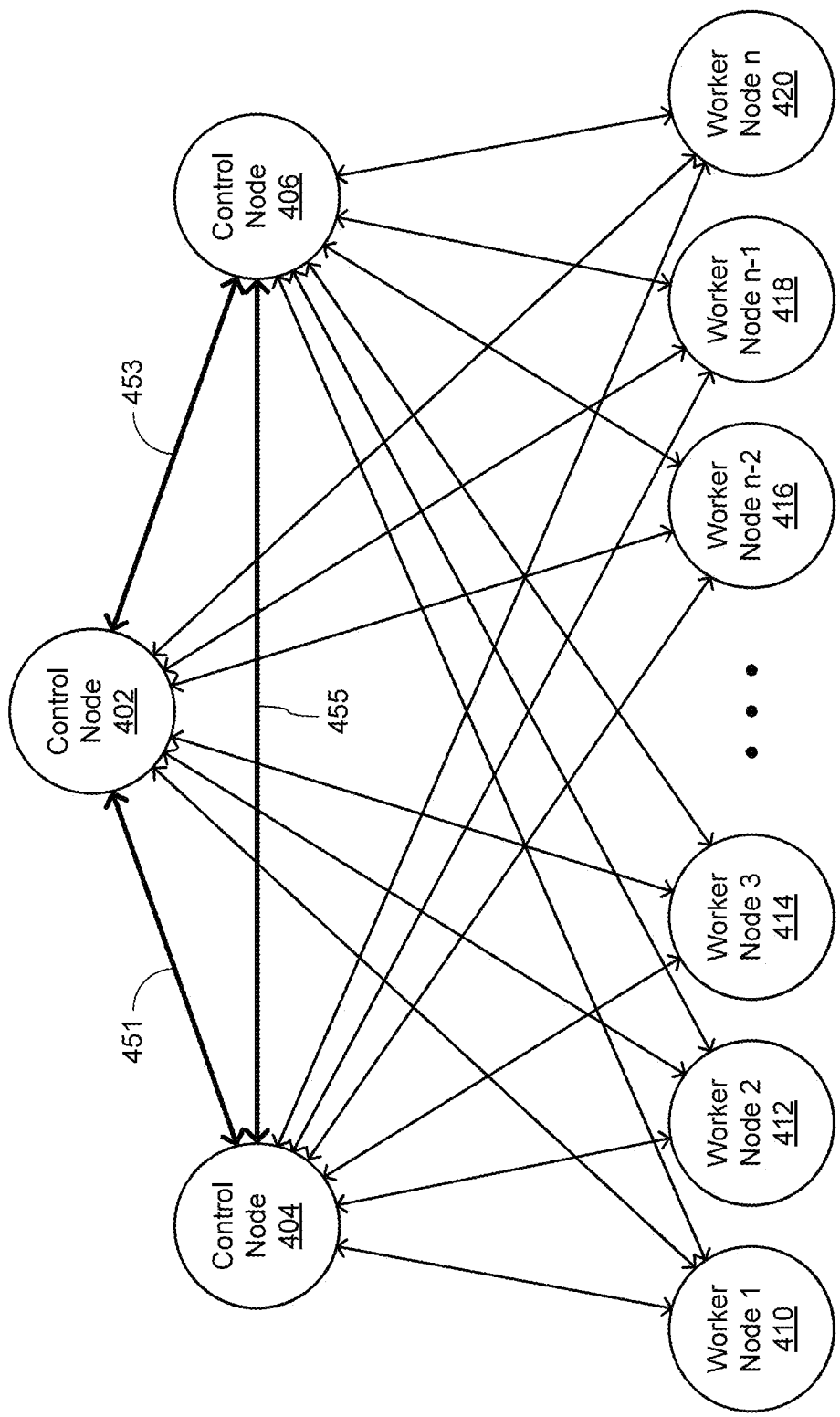
FIG. 4 shows a communications grid computing system including a variety of control and worker nodes according to some aspects of the present disclosure.

FIG. 4 illustrates a communications grid computing system 400 including a variety of control and worker nodes, according to embodiments of the present technology. Communications grid computing system 400 includes three control nodes and one or more worker nodes. Communications grid computing system 400 includes control nodes 402, 404, and 406. The control nodes are communicatively connected via communication paths 451, 453, and 455. Therefore, the control nodes may transmit information (e.g., related to the communications grid or notifications), to and receive information from each other. Although communications grid computing system 400 is shown in FIG. 4 as including three control nodes, the communications grid may include more or less than three control nodes.

Communications grid computing system (or just "communications grid") 400 also includes one or more worker nodes. Shown in FIG. 4 are six worker nodes 410-420. Although FIG. 4 shows six worker nodes, a communications grid according to embodiments of the present technology may include more or less than six worker nodes. The number of worker nodes included in a communications grid may be dependent upon how large the project or data set is being processed by the communications grid, the capacity of each worker node, the time designated for the communications grid to complete the project, among others. Each worker node within the communications grid 400 may be connected (wired or wirelessly, and directly or indirectly) to control nodes 402-406. Therefore, each worker node may receive information from the control nodes (e.g., an instruction to perform work on a project) and may transmit information to the control nodes (e.g., a result from work performed on a project). Furthermore, worker nodes may communicate with each other (either directly or indirectly). For example, worker nodes may transmit data between each other related to a job being performed or an individual task within a job being performed by that worker node. However, in certain embodiments, worker nodes may not, for example, be connected (communicatively or otherwise) to certain other worker nodes. In an embodiment, worker nodes may only be able to communicate with the control node that controls it, and may not be able to communicate with other worker nodes in the communications grid, whether they are other worker nodes controlled by the control node that controls the worker node, or worker nodes that are controlled by other control nodes in the communications grid.

A control node may connect with an external device with which the control node may communicate (e.g., a grid user, such as a server or computer, may connect to a controller of the grid). For example, a server or computer may connect to control nodes and may transmit a project or job to the node. The project may include a data set. The data set may be of any size. Once the control node receives such a project including a large data set, the control node may distribute the data set or projects related to the data set to be performed by worker nodes. Alternatively, for a project including a large data set, the data set may be received or stored by a machine other than a control node (e.g., a HADOOP® standard-compliant data node employing the HADOOP® Distributed File System, or HDFS).

Control nodes may maintain knowledge of the status of the nodes in the grid (i.e., grid status information), accept work requests from clients, subdivide the work across worker nodes, and coordinate the worker nodes, among other responsibilities. Worker nodes may accept work requests from a control node and provide the control node with results of the work performed by the worker node. A grid may be started from a single node (e.g., a machine, computer, server, etc.). This first node may be assigned or may start as the primary control node that will control any additional nodes that enter the grid.

When a project is submitted for execution (e.g., by a client or a controller of the grid) it may be assigned to a set of nodes. After the nodes are assigned to a project, a data structure (i.e., a communicator) may be created. The communicator may be used by the project for information to be shared between the project codes running on each node. A communication handle may be created on each node. A handle, for example, is a reference to the communicator that is valid within a single process on a single node, and the handle may be used when requesting communications between nodes.

A control node, such as control node 402, may be designated as the primary control node. A server, computer or other external device may connect to the primary control node. Once the control node receives a project, the primary control node may distribute portions of the project to its worker nodes for execution. For example, when a project is initiated on communications grid 400, primary control node 402 controls the work to be performed for the project in order to complete the project as requested or instructed. The primary control node may distribute work to the worker nodes based on various factors, such as which subsets or portions of projects may be completed most efficiently and in the correct amount of time. For example, a worker node may perform analysis on a portion of data that is already local to (e.g., stored on) the worker node. The primary control node also coordinates and processes the results of the work performed by each worker node after each worker node executes and completes its job. For example, the primary control node may receive a result from one or more worker nodes, and the control node may organize (e.g., collect and assemble) the results received and compile them to produce a complete result for the project received from the end user.

Any remaining control nodes, such as control nodes 404 and 406, may be assigned as backup control nodes for the project. In an embodiment, backup control nodes may not control any portion of the project. Instead, backup control nodes may serve as a backup for the primary control node and take over as primary control node if the primary control node were to fail. If a communications grid were to include only a single control node, and the control node were to fail (e.g., the control node is shut off or breaks), then the communications grid as a whole may fail and any project or job being run on the communications grid may fail and may not complete. While the project may be run again, such a failure may cause a delay (severe delay in some cases, such as overnight delay) in completion of the project. Therefore, a grid with multiple control nodes, including a backup control node, may be beneficial.

To add another node or machine to the grid, the primary control node may open a pair of listening sockets, for example. A socket may be used to accept work requests from clients, and the second socket may be used to accept connections from other grid nodes. The primary control node may be provided with a list of other nodes (e.g., other machines, computers, servers) that will participate in the grid, and the role that each node will fill in the grid. Upon startup of the primary control node (e.g., the first node on the grid), the primary control node may use a network protocol to start the server process on every other node in the grid. Command line parameters, for example, may inform each node of one or more pieces of information, such as: the role that the node will have in the grid, the host name of the primary control node, and the port number on which the primary control node is accepting connections from peer nodes, among others. The information may also be provided in a configuration file, transmitted over a secure shell tunnel, or received from a configuration server, among others. While the other machines in the grid may not initially know about the configuration of the grid, that information may also be sent to each other node by the primary control node. Updates of the grid information may also be subsequently sent to those nodes.

For any control node other than the primary control node added to the grid, the control node may open three sockets. The first socket may accept work requests from clients, the second socket may accept connections from other grid members, and the third socket may connect (e.g., permanently) to the primary control node. When a control node (e.g., primary control node) receives a connection from another control node, it first checks to see if the peer node is in the list of configured nodes in the grid. If it is not on the list, the control node may clear the connection. If it is on the list, it may then attempt to authenticate the connection. If authentication is successful, the authenticating node may transmit information to its peer, such as the port number on which a node is listening for connections, the host name of the node, and information about how to authenticate the node, among other information. When a node, such as the new control node, receives information about another active node, it will check to see if it already has a connection to that other node. If it does not have a connection to that node, it may then establish a connection to that control node.

Any worker node added to the grid may establish a connection to the primary control node and any other control nodes on the grid. After establishing the connection, it may authenticate itself to the grid (e.g., any control nodes, including both primary and backup, or a server or user controlling the grid). After successful authentication, the worker node may accept configuration information from the control node.

When a node joins a communications grid (e.g., when the node is powered on or connected to an existing node on the grid or both), the node is assigned (e.g., by an operating system of the grid) a universally unique identifier (UUID). This unique identifier may help other nodes and external entities (devices, users, etc.) to identify the node and distinguish it from other nodes. When a node is connected to the grid, the node may share its unique identifier with the other nodes in the grid. Since each node may share its unique identifier, each node may know the unique identifier of every other node on the grid. Unique identifiers may also designate a hierarchy of each of the nodes (e.g., backup control nodes) within the grid. For example, the unique identifiers of each of the backup control nodes may be stored in a list of backup control nodes to indicate an order in which the backup control nodes will take over for a failed primary control node to become a new primary control node. However, a hierarchy of nodes may also be determined using methods other than using the unique identifiers of the nodes. For example, the hierarchy may be predetermined, or may be assigned based on other predetermined factors.

The grid may add new machines at any time (e.g., initiated from any control node). Upon adding a new node to the grid, the control node may first add the new node to its table of grid nodes. The control node may also then notify every other control node about the new node. The nodes receiving the notification may acknowledge that they have updated their configuration information.

Primary control node 402 may, for example, transmit one or more communications to backup control nodes 404 and 406 (and, for example, to other control or worker nodes within the communications grid). Such communications may be sent periodically, at fixed time intervals, between known fixed stages of the project's execution, among other protocols. The communications transmitted by primary control node 402 may be of varied types and may include a variety of types of information. For example, primary control node 402 may transmit snapshots (e.g., status information) of the communications grid so that backup control node 404 always has a recent snapshot of the communications grid. The snapshot or grid status may include, for example, the structure of the grid (including, for example, the worker nodes in the grid, unique identifiers of the nodes, or their relationships with the primary control node) and the status of a project (including, for example, the status of each worker node's portion of the project). The snapshot may also include analysis or results received from worker nodes in the communications grid. The backup control nodes may receive and store the backup data received from the primary control node. The backup control nodes may transmit a request for such a snapshot (or other information) from the primary control node, or the primary control node may send such information periodically to the backup control nodes.

As noted, the backup data may allow the backup control node to take over as primary control node if the primary control node fails without requiring the grid to start the project over from scratch. If the primary control node fails, the backup control node that will take over as primary control node may retrieve the most recent version of the snapshot received from the primary control node and use the snapshot to continue the project from the stage of the project indicated by the backup data. This may prevent failure of the project as a whole.

A backup control node may use various methods to determine that the primary control node has failed. In one example of such a method, the primary control node may transmit (e.g., periodically) a communication to the backup control node that indicates that the primary control node is working and has not failed, such as a heartbeat communication. The backup control node may determine that the primary control node has failed if the backup control node has not received a heartbeat communication for a certain predetermined period of time. Alternatively, a backup control node may also receive a communication from the primary control node itself (before it failed) or from a worker node that the primary control node has failed, for example because the primary control node has failed to communicate with the worker node.

Different methods may be performed to determine which backup control node of a set of backup control nodes (e.g., backup control nodes 404 and 406) will take over for failed primary control node 402 and become the new primary control node. For example, the new primary control node may be chosen based on a ranking or "hierarchy" of backup control nodes based on their unique identifiers. In an alternative embodiment, a backup control node may be assigned to be the new primary control node by another device in the communications grid or from an external device (e.g., a system infrastructure or an end user, such as a server or computer, controlling the communications grid). In another alternative embodiment, the backup control node that takes over as the new primary control node may be designated based on bandwidth or other statistics about the communications grid.

A worker node within the communications grid may also fail. If a worker node fails, work being performed by the failed worker node may be redistributed amongst the operational worker nodes. In an alternative embodiment, the primary control node may transmit a communication to each of the operable worker nodes still on the communications grid that each of the worker nodes should purposefully fail also. After each of the worker nodes fail, they may each retrieve their most recent saved checkpoint of their status and re-start the project from that checkpoint to minimize lost progress on the project being executed.

Figure 5:
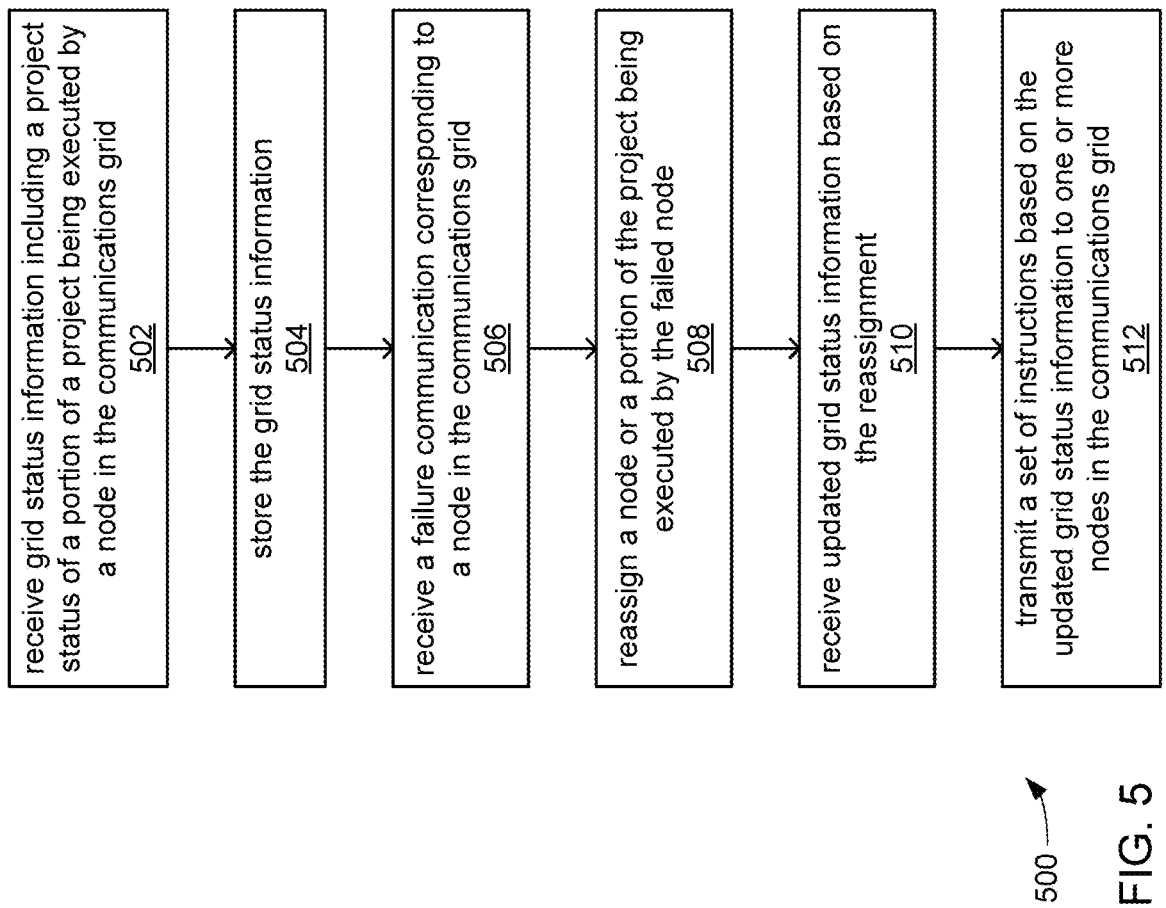
FIG. 5 shows a flow chart showing an example process for adjusting a communications grid or a work project in a communications grid after a failure of a node according to some aspects of the present disclosure.

FIG. 5 illustrates a flow chart showing an example process 500 for adjusting a communications grid or a work project in a communications grid after a failure of a node, according to embodiments of the present technology. The process may include, for example, receiving grid status information including a project status of a portion of a project being executed by a node in the communications grid, as described in operation 502. For example, a control node (e.g., a backup control node connected to a primary control node and a worker node on a communications grid) may receive grid status information, where the grid status information includes a project status of the primary control node or a project status of the worker node. The project status of the primary control node and the project status of the worker node may include a status of one or more portions of a project being executed by the primary and worker nodes in the communications grid. The process may also include storing the grid status information, as described in operation 504. For example, a control node (e.g., a backup control node) may store the received grid status information locally within the control node. Alternatively, the grid status information may be sent to another device for storage where the control node may have access to the information.

The process may also include receiving a failure communication corresponding to a node in the communications grid in operation 506. For example, a node may receive a failure communication including an indication that the primary control node has failed, prompting a backup control node to take over for the primary control node. In an alternative embodiment, a node may receive a failure that a worker node has failed, prompting a control node to reassign the work being performed by the worker node. The process may also include reassigning a node or a portion of the project being executed by the failed node, as described in operation 508. For example, a control node may designate the backup control node as a new primary control node based on the failure communication upon receiving the failure communication. If the failed node is a worker node, a control node may identify a project status of the failed worker node using the snapshot of the communications grid, where the project status of the failed worker node includes a status of a portion of the project being executed by the failed worker node at the failure time.

The process may also include receiving updated grid status information based on the reassignment, as described in operation 510, and transmitting a set of instructions based on the updated grid status information to one or more nodes in the communications grid, as described in operation 512. The updated grid status information may include an updated project status of the primary control node or an updated project status of the worker node. The updated information may be transmitted to the other nodes in the grid to update their stale stored information.

Figure 6:
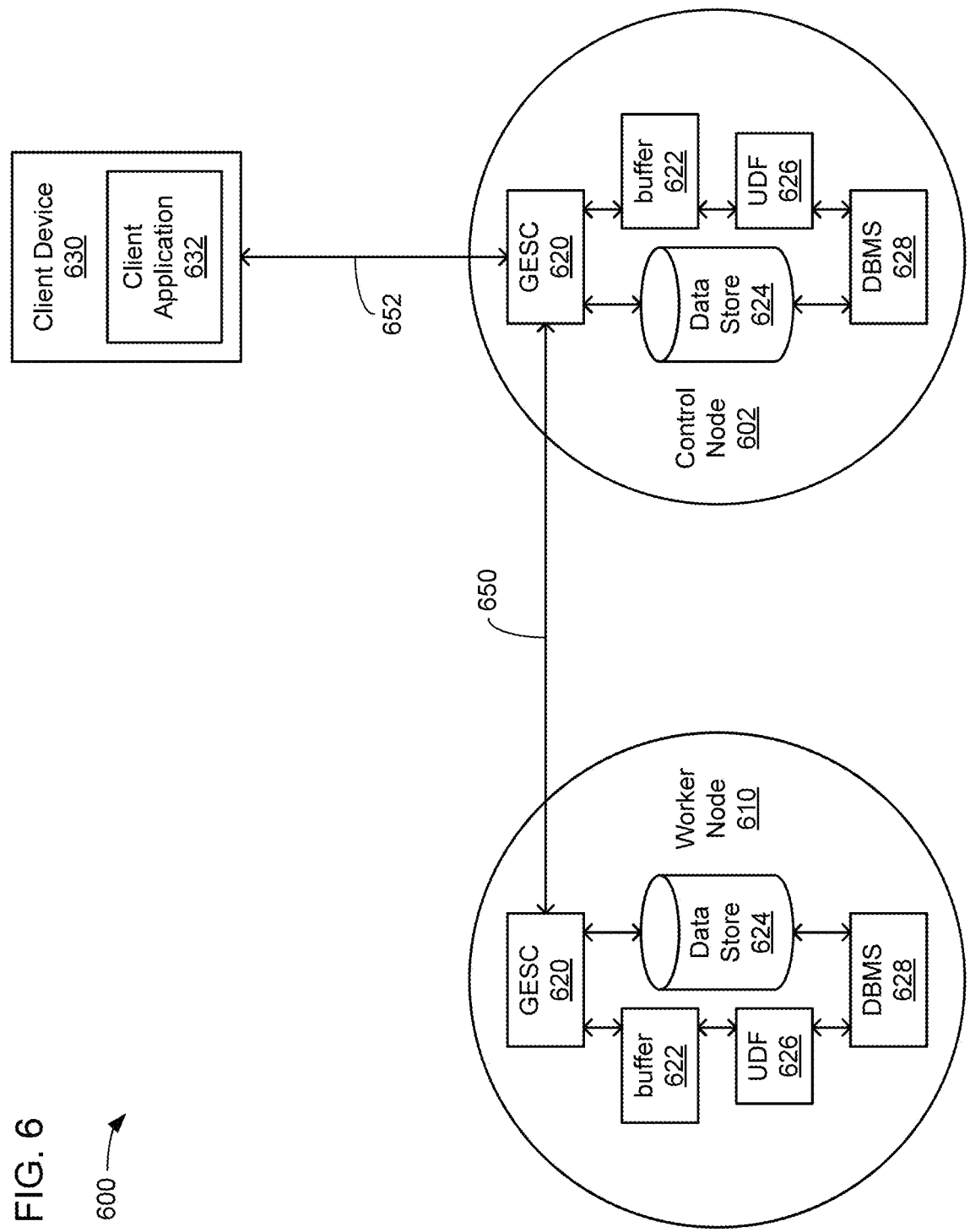
FIG. 6 shows a portion of a communications grid computing system including a control node and a worker node according to some aspects of the present disclosure.

FIG. 6 illustrates a portion of a communications grid computing system 600 including a control node and a worker node, according to embodiments of the present technology. Communications grid computing system 600 includes one control node (control node 602) and one worker node (worker node 610) for purposes of illustration, but may include more worker and/or control nodes. The control node 602 is communicatively connected to worker node 610 via communication path 650. Therefore, control node 602 may transmit information (e.g., related to the communications grid or notifications), to and receive information from worker node 610 via path 650.

Similar to in FIG. 4, communications grid computing system (or just "communications grid") 600 includes data processing nodes (control node 602 and worker node 610). Nodes 602 and 610 include multi-core data processors. Each node 602 and 610 includes a grid-enabled software component (GESC) 620 that executes on the data processor associated with that node and interfaces with buffer memory 622 also associated with that node. Each node 602 and 610 includes database management software (DBMS) 628 that executes on a database server (not shown) at control node 602 and on a database server (not shown) at worker node 610.

Each node also includes a data store 624. Data stores 624, similar to network-attached data stores 110 in FIG. 1 and data stores 235 in FIG. 2, are used to store data to be processed by the nodes in the computing environment. Data stores 624 may also store any intermediate or final data generated by the computing system after being processed, for example in non-volatile memory. However in certain embodiments, the configuration of the grid computing environment allows its operations to be performed such that intermediate and final data results can be stored solely in volatile memory (e.g., RAM), without a requirement that intermediate or final data results be stored to non-volatile types of memory. Storing such data in volatile memory may be useful in certain situations, such as when the grid receives queries (e.g., ad hoc) from a client and when responses, which are generated by processing large amounts of data, need to be generated quickly or on-the-fly. In such a situation, the grid may be configured to retain the data within memory so that responses can be generated at different levels of detail and so that a client may interactively query against this information.

Each node also includes a user-defined function (UDF) 626. The UDF provides a mechanism for the DBMS 628 to transfer data to or receive data from the database stored in the data stores 624 that are managed by the DBMS 628. For example, UDF 626 can be invoked by the DBMS 628 to provide data to the GESC 620 for processing. The UDF 626 may establish a socket connection (not shown) with the GESC 620 to transfer the data. Alternatively, the UDF 626 can transfer data to the GESC 620 by writing data to shared memory accessible by both the UDF 626 and the GESC 620

The GESC 620 at the nodes 602 and 610 may be connected via a network, such as network 108 shown in FIG. 1. Therefore, nodes 602 and 610 can communicate with each other via the network using a predetermined communication protocol such as, for example, the Message Passing Interface (MPI). Each GESC 620 can engage in point-to-point communication with the GESC at another node or in collective communication with multiple GESCs via the network. The GESC 620 at each node may contain identical (or nearly identical) software instructions. Each node may be capable of operating as either a control node or a worker node. The GESC at the control node 602 can communicate, over a communication path 652, with a client device 630. More specifically, control node 602 may communicate with client application 632 hosted by the client device 630 to receive queries and to respond to those queries after processing large amounts of data.

DBMS 628 may control the creation, maintenance, and use of database or data structure (not shown) within a nodes 602 or 610. The database may organize data stored in data stores 624. The DBMS 628 at control node 602 may accept requests for data and transfer the appropriate data for the request. With such a process, collections of data may be distributed across multiple physical locations. In this example, each node 602 and 610 stores a portion of the total data managed by the management system in its associated data store 624.

Furthermore, the DBMS may be responsible for protecting against data loss using replication techniques. Replication includes providing a backup copy of data stored on one node on one or more other nodes. Therefore, if one node fails, the data from the failed node can be recovered from a replicated copy residing at another node. However, as described herein with respect to FIG. 4, data or status information for each node in the communications grid may also be shared with each node on the grid.

Figure 7:
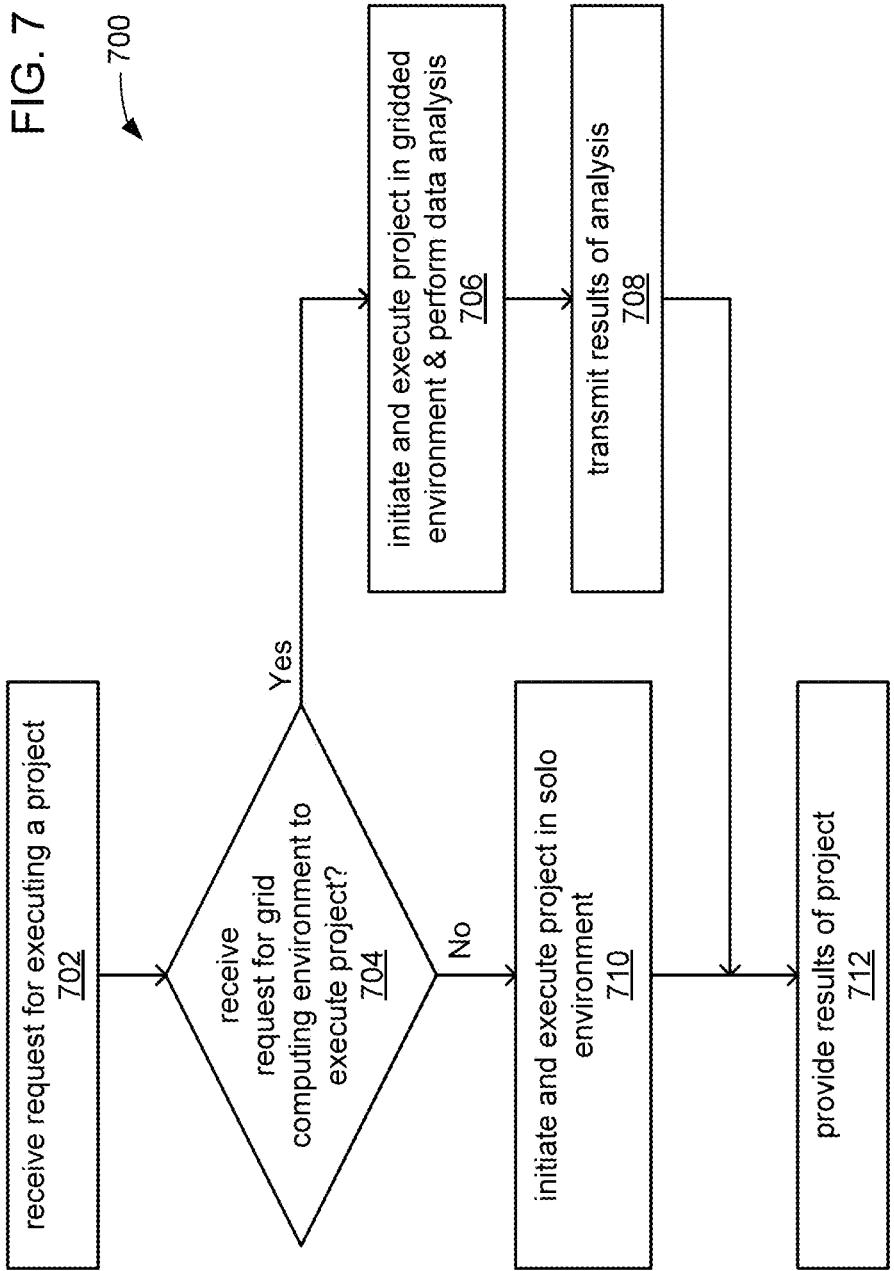
FIG. 7 shows a flow chart showing an example method 700 for executing a project within a grid computing system according to some aspects of the present disclosure.

FIG. 7 illustrates a flow chart showing an example method 700 for executing a project within a grid computing system, according to embodiments of the present technology. As described with respect to FIG. 6, the GESC at the control node may transmit data with a client device (e.g., client device 630) to receive queries for executing a project and to respond to those queries after large amounts of data have been processed. The query may be transmitted to the control node, where the query may include a request for executing a project, as described in operation 702. The query can contain instructions on the type of data analysis to be performed in the project and whether the project should be executed using the grid-based computing environment, as shown in operation 704.

To initiate the project, the control node may determine if the query requests use of the grid-based computing environment to execute the project. If the determination is no, then the control node initiates execution of the project in a solo environment (e.g., at the control node), as described in operation 710. If the determination is yes, the control node may initiate execution of the project in the grid-based computing environment, as described in operation 706. In such a situation, the request may include a requested configuration of the grid. For example, the request may include a number of control nodes and a number of worker nodes to be used in the grid when executing the project. After the project has been completed, the control node may transmit results of the analysis yielded by the grid, as described in operation 708. Whether the project is executed in a solo or grid-based environment, the control node provides the results of the project, as described in operation 712.

As noted with respect to FIG. 2, the computing environments described herein may collect data (e.g., as received from network devices, such as sensors, such as network devices 204-209 in FIG. 2, and client devices or other sources) to be processed as part of a data analytics project, and data may be received in real time as part of a streaming analytics environment (e.g., ESP). Data may be collected using a variety of sources as communicated via different kinds of networks or locally, such as on a real-time streaming basis. For example, network devices may receive data periodically from network device sensors as the sensors continuously sense, monitor and track changes in their environments. More specifically, an increasing number of distributed applications develop or produce continuously flowing data from distributed sources by applying queries to the data before distributing the data to geographically distributed recipients. An event stream processing engine (ESPE) may continuously apply the queries to the data as it is received and determines which entities should receive the data. Client or other devices may also subscribe to the ESPE or other devices processing ESP data so that they can receive data after processing, based on for example the entities determined by the processing engine. For example, client devices 230 in FIG. 2 may subscribe to the ESPE in computing environment 214. In another example, event subscription devices 1024*a*-*c*, described further with respect to FIG. 10, may also subscribe to the ESPE. The ESPE may determine or define how input data or event streams from network devices or other publishers (e.g., network devices 204-209 in FIG. 2) are transformed into meaningful output data to be consumed by subscribers, such as for example client devices 230 in FIG. 2.

FIG. 8 illustrates a block diagram including components of an Event Stream Processing Engine (ESPE), according to embodiments of the present technology. ESPE 800 may include one or more projects 802. A project may be described as a second-level container in an engine model managed by ESPE 800 where a thread pool size for the project may be defined by a user. Each project of the one or more projects 802 may include one or more continuous queries 804 that contain data flows, which are data transformations of incoming event streams. The one or more continuous queries 804 may include one or more source windows 806 and one or more derived windows 808.

The ESPE may receive streaming data over a period of time related to certain events, such as events or other data sensed by one or more network devices. The ESPE may perform operations associated with processing data created by the one or more devices. For example, the ESPE may receive data from the one or more network devices 204-209 shown in FIG. 2. As noted, the network devices may include sensors that sense different aspects of their environments, and may collect data over time based on those sensed observations. For example, the ESPE may be implemented within one or more of machines 220 and 240 shown in FIG. 2. The ESPE may be implemented within such a machine by an ESP application. An ESP application may embed an ESPE with its own dedicated thread pool or pools into its application space where the main application thread can do application-specific work and the ESPE processes event streams at least by creating an instance of a model into processing objects.

The engine container is the top-level container in a model that manages the resources of the one or more projects 802. In an illustrative embodiment, for example, there may be only one ESPE 800 for each instance of the ESP application, and ESPE 800 may have a unique engine name. Additionally, the one or more projects 802 may each have unique project names, and each query may have a unique continuous query name and begin with a uniquely named source window of the one or more source windows 806. ESPE 800 may or may not be persistent.

Continuous query modeling involves defining directed graphs of windows for event stream manipulation and transformation. A window in the context of event stream manipulation and transformation is a processing node in an event stream processing model. A window in a continuous query can perform aggregations, computations, pattern-matching, and other operations on data flowing through the window. A continuous query may be described as a directed graph of source, relational, pattern matching, and procedural windows. The one or more source windows 806 and the one or more derived windows 808 represent continuously executing queries that generate updates to a query result set as new event blocks stream through ESPE 800. A directed graph, for example, is a set of nodes connected by edges, where the edges have a direction associated with them.

An event object may be described as a packet of data accessible as a collection of fields, with at least one of the fields defined as a key or unique identifier (ID). The event object may be created using a variety of formats including binary, alphanumeric, XML, etc. Each event object may include one or more fields designated as a primary identifier (ID) for the event so ESPE 800 can support operation codes (opcodes) for events including insert, update, upsert, and delete. Upsert opcodes update the event if the key field already exists; otherwise, the event is inserted. For illustration, an event object may be a packed binary representation of a set of field values and include both metadata and field data associated with an event. The metadata may include an opcode indicating if the event represents an insert, update, delete, or upsert, a set of flags indicating if the event is a normal, partial-update, or a retention generated event from retention policy management, and a set of microsecond timestamps that can be used for latency measurements.

An event block object may be described as a grouping or package of event objects. An event stream may be described as a flow of event block objects. A continuous query of the one or more continuous queries 804 transforms a source event stream made up of streaming event block objects published into ESPE 800 into one or more output event streams using the one or more source windows 806 and the one or more derived windows 808. A continuous query can also be thought of as data flow modeling.

The one or more source windows 806 are at the top of the directed graph and have no windows feeding into them. Event streams are published into the one or more source windows 806, and from there, the event streams may be directed to the next set of connected windows as defined by the directed graph. The one or more derived windows 808 are all instantiated windows that are not source windows and that have other windows streaming events into them. The one or more derived windows 808 may perform computations or transformations on the incoming event streams. The one or more derived windows 808 transform event streams based on the window type (that is operators such as join, filter, compute, aggregate, copy, pattern match, procedural, union, etc.) and window settings. As event streams are published into ESPE 800, they are continuously queried, and the resulting sets of derived windows in these queries are continuously updated.

FIG. 9 illustrates a flow chart showing an example process including operations performed by an event stream processing engine, according to some embodiments of the present technology. As noted, the ESPE 800 (or an associated ESP application) defines how input event streams are transformed into meaningful output event streams. More specifically, the ESP application may define how input event streams from publishers (e.g., network devices providing sensed data) are transformed into meaningful output event streams consumed by subscribers (e.g., a data analytics project being executed by a machine or set of machines).

Within the application, a user may interact with one or more user interface windows presented to the user in a display under control of the ESPE independently or through a browser application in an order selectable by the user. For example, a user may execute an ESP application, which causes presentation of a first user interface window, which may include a plurality of menus and selectors such as drop down menus, buttons, text boxes, hyperlinks, etc. associated with the ESP application as understood by a person of skill in the art. As further understood by a person of skill in the art, various operations may be performed in parallel, for example, using a plurality of threads.

At operation 900, an ESP application may define and start an ESPE, thereby instantiating an ESPE at a device, such as machine 220 and/or 240. In an operation 902, the engine container is created. For illustration, ESPE 800 may be instantiated using a function call that specifies the engine container as a manager for the model.

In an operation 904, the one or more continuous queries 804 are instantiated by ESPE 800 as a model. The one or more continuous queries 804 may be instantiated with a dedicated thread pool or pools that generate updates as new events stream through ESPE 800. For illustration, the one or more continuous queries 804 may be created to model business processing logic within ESPE 800, to predict events within ESPE 800, to model a physical system within ESPE 800, to predict the physical system state within ESPE 800, etc. For example, as noted, ESPE 800 may be used to support sensor data monitoring and management (e.g., sensing may include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, or electrical current, etc.).

ESPE 800 may analyze and process events in motion or "event streams." Instead of storing data and running queries against the stored data, ESPE 800 may store queries and stream data through them to allow continuous analysis of data as it is received. The one or more source windows 806 and the one or more derived windows 808 may be created based on the relational, pattern matching, and procedural algorithms that transform the input event streams into the output event streams to model, simulate, score, test, predict, etc. based on the continuous query model defined and application to the streamed data.

In an operation 906, a publish/subscribe (pub/sub) capability is initialized for ESPE 800. In an illustrative embodiment, a pub/sub capability is initialized for each project of the one or more projects 802. To initialize and enable pub/sub capability for ESPE 800, a port number may be provided. Pub/sub clients can use a host name of an ESP device running the ESPE and the port number to establish pub/sub connections to ESPE 800.

FIG. 10 illustrates an ESP system 1000 interfacing between publishing device 1022 and event subscribing devices 1024a-c, according to embodiments of the present technology. ESP system 1000 may include ESP device or subsystem 1001, event publishing device 1022, an event subscribing device A 1024a, an event subscribing device B 1024b, and an event subscribing device C 1024c. Input event streams are output to ESP subsystem 1001 by publishing device 1022. In alternative embodiments, the input event streams may be created by a plurality of publishing devices. The plurality of publishing devices further may publish event streams to other ESP devices. The one or more continuous queries instantiated by ESPE 800 may analyze and process the input event streams to form output event streams output to event subscribing device A 1024a, event subscribing device B 1024b, and event subscribing device C 1024c. ESP system 1000 may include a greater or a fewer number of event subscribing devices of event subscribing devices.

Publish-subscribe is a message-oriented interaction paradigm based on indirect addressing. Processed data recipients specify their interest in receiving information from ESPE 800 by subscribing to specific classes of events, while information sources publish events to ESPE 800 without directly addressing the receiving parties. ESPE 800 coordinates the interactions and processes the data. In some cases, the data source receives confirmation that the published information has been received by a data recipient.

A publish/subscribe API may be described as a library that enables an event publisher, such as publishing device 1022, to publish event streams into ESPE 800 or an event subscriber, such as event subscribing device A 1024a, event subscribing device B 1024b, and event subscribing device C 1024c, to subscribe to event streams from ESPE 800. For illustration, one or more publish/subscribe APIs may be defined. Using the publish/subscribe API, an event publishing application may publish event streams into a running event stream processor project source window of ESPE 800, and the event subscription application may subscribe to an event stream processor project source window of ESPE 800.

The publish/subscribe API provides cross-platform connectivity and endianness compatibility between ESP application and other networked applications, such as event publishing applications instantiated at publishing device 1022, and event subscription applications instantiated at one or more of event subscribing device A 1024*a*, event subscribing device B 1024*b*, and event subscribing device C 1024*c*.

Referring back to FIG. 9, operation 906 initializes the publish/subscribe capability of ESPE 800. In an operation 908, the one or more projects 802 are started. The one or more started projects may run in the background on an ESP device. In an operation 910, an event block object is received from one or more computing device of the event publishing device 1022.

ESP subsystem 1001 may include a publishing client 1002, ESPE 800, a subscribing client A 1004, a subscribing client B 1006, and a subscribing client C 1008. Publishing client 1002 may be started by an event publishing application executing at publishing device 1022 using the publish/subscribe API. Subscribing client A 1004 may be started by an event subscription application A, executing at event subscribing device A 1024*a* using the publish/subscribe API. Subscribing client B 1006 may be started by an event subscription application B executing at event subscribing device B 1024*b* using the publish/subscribe API. Subscribing client C 1008 may be started by an event subscription application C executing at event subscribing device C 1024*c* using the publish/subscribe API.

An event block object containing one or more event objects is injected into a source window of the one or more source windows 806 from an instance of an event publishing application on event publishing device 1022. The event block object may be generated, for example, by the event publishing application and may be received by publishing client 1002. A unique ID may be maintained as the event block object is passed between the one or more source windows 806 and/or the one or more derived windows 808 of ESPE 800, and to subscribing client A 1004, subscribing client B 1006, and subscribing client C 1008 and to event subscription device A 1024*a*, event subscription device B 1024*b*, and event subscription device C 1024*c*. Publishing client 1002 may further generate and include a unique embedded transaction ID in the event block object as the event block object is processed by a continuous query, as well as the unique ID that publishing device 1022 assigned to the event block object.

In an operation 912, the event block object is processed through the one or more continuous queries 804. In an operation 914, the processed event block object is output to one or more computing devices of the event subscribing devices 1024*a-c*. For example, subscribing client A 1004, subscribing client B 1006, and subscribing client C 1008 may send the received event block object to event subscription device A 1024*a*, event subscription device B 1024*b*, and event subscription device C 1024*c*, respectively.

ESPE 800 maintains the event block containership aspect of the received event blocks from when the event block is published into a source window and works its way through the directed graph defined by the one or more continuous queries 804 with the various event translations before being output to subscribers. Subscribers can correlate a group of subscribed events back to a group of published events by comparing the unique ID of the event block object that a publisher, such as publishing device 1022, attached to the event block object with the event block ID received by the subscriber.

In an operation 916, a determination is made concerning whether or not processing is stopped. If processing is not stopped, processing continues in operation 910 to continue receiving the one or more event streams containing event block objects from the, for example, one or more network devices. If processing is stopped, processing continues in an operation 918. In operation 918, the started projects are stopped. In operation 920, the ESPE is shutdown.

As noted, in some embodiments, big data is processed for an analytics project after the data is received and stored. In other embodiments, distributed applications process continuously flowing data in real-time from distributed sources by applying queries to the data before distributing the data to geographically distributed recipients. As noted, an event stream processing engine (ESPE) may continuously apply the queries to the data as it is received and determines which entities receive the processed data. This allows for large amounts of data being received and/or collected in a variety of environments to be processed and distributed in real time. For example, as shown with respect to FIG. 2, data may be collected from network devices that may include devices within the internet of things, such as devices within a home automation network. However, such data may be collected from a variety of different resources in a variety of different environments. In any such situation, embodiments of the present technology allow for real-time processing of such data.

Aspects of the current disclosure provide technical solutions to technical problems, such as computing problems that arise when an ESP device fails which results in a complete service interruption and potentially significant data loss. The data loss can be catastrophic when the streamed data is supporting mission critical operations such as those in support of an ongoing manufacturing or drilling operation. An embodiment of an ESP system achieves a rapid and seamless failover of ESPE running at the plurality of ESP devices without service interruption or data loss, thus significantly improving the reliability of an operational system that relies on the live or real-time processing of the data streams. The event publishing systems, the event subscribing systems, and each ESPE not executing at a failed ESP device are not aware of or effected by the failed ESP device. The ESP system may include thousands of event publishing systems and event subscribing systems. The ESP system keeps the failover logic and awareness within the boundaries of out-messaging network connector and out-messaging network device.

In one example embodiment, a system is provided to support a failover when event stream processing (ESP) event blocks. The system includes, but is not limited to, an out-messaging network device and a computing device. The computing device includes, but is not limited to, a processor and a computer-readable medium operably coupled to the processor. The processor is configured to execute an ESP engine (ESPE). The computer-readable medium has instructions stored thereon that, when executed by the processor, cause the computing device to support the failover. An event block object is received from the ESPE that includes a unique identifier. A first status of the computing device as active or standby is determined. When the first status is active, a second status of the computing device as newly active or not newly active is determined. Newly active is determined when the computing device is switched from a standby status to an active status. When the second status is newly active, a last published event block object identifier that uniquely identifies a last published event block object is determined. A next event block object is selected from a non-transitory computer-readable medium accessible by the computing device. The next event block object has an event block object identifier that is greater than the determined last published event block object identifier. The selected next event block object is published to an out-messaging network device. When the second status of the computing device is not newly active, the received event block object is published to the out-messaging network device. When the first status of the computing device is standby, the received event block object is stored in the non-transitory computer-readable medium.

Figure 11:
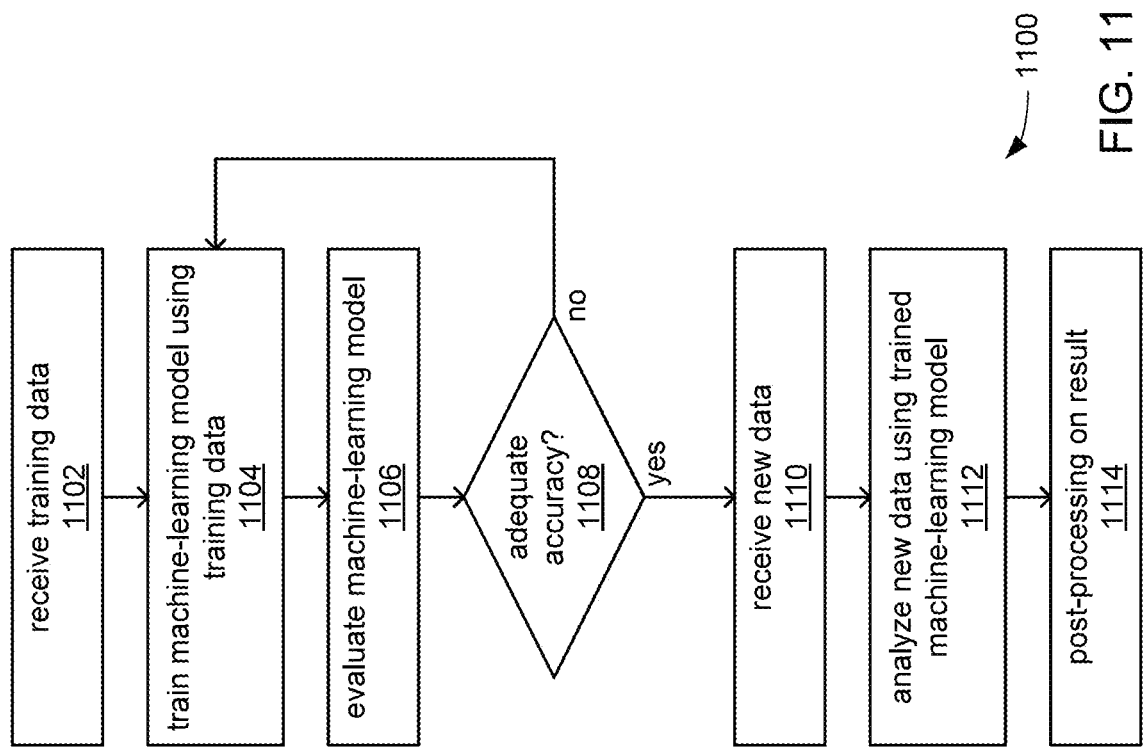
FIG. 11 shows a flow chart of an example of a process for generating and using a machine-learning model according to some aspects of the present disclosure.

FIG. 11 is a flow chart of an example of a process for generating and using a machine-learning model according to some aspects. Machine learning is a branch of artificial intelligence that relates to mathematical models that can learn from, categorize, and make predictions about data. Such mathematical models, which can be referred to as machine-learning models, can classify input data among two or more classes; cluster input data among two or more groups; predict a result based on input data; identify patterns or trends in input data; identify a distribution of input data in a space; or any combination of these. Examples of machine-learning models can include (i) neural networks; (ii) decision trees, such as classification trees and regression trees; (iii) classifiers, such as Naïve bias classifiers, logistic regression classifiers, ridge regression classifiers, random forest classifiers, least absolute shrinkage and selector (LASSO) classifiers, and support vector machines; (iv) clusterers, such as k-means clusterers, mean-shift clusterers, and spectral clusterers; (v) factorizers, such as factorization machines, principal component analyzers and kernel principal component analyzers; and (vi) ensembles or other combinations of machine-learning models. In some examples, neural networks can include deep neural networks, feed-forward neural networks, recurrent neural networks, convolutional neural networks, radial basis function (RBF) neural networks, echo state neural networks, long short-term memory neural networks, bi-directional recurrent neural networks, gated neural networks, hierarchical recurrent neural networks, stochastic neural networks, modular neural networks, spiking neural networks, dynamic neural networks, cascading neural networks, neuro-fuzzy neural networks, or any combination of these.

Different machine-learning models may be used interchangeably to perform a task. Examples of tasks that can be performed at least partially using machine-learning models include various types of scoring; bioinformatics; cheminformatics; software engineering; fraud detection; customer segmentation; generating online recommendations; adaptive websites; determining customer lifetime value; search engines; placing advertisements in real time or near real time; classifying DNA sequences; affective computing; performing natural language processing and understanding; object recognition and computer vision; robotic locomotion; playing games; optimization and metaheuristics; detecting network intrusions; medical diagnosis and monitoring; or predicting when an asset, such as a machine, will need maintenance.

Any number and combination of tools can be used to create machine-learning models. Examples of tools for creating and managing machine-learning models can include SAS® Enterprise Miner, SAS® Rapid Predictive Modeler, and SAS® Model Manager, SAS Cloud Analytic Services (CAS)®, SAS Viya® of all which are by SAS Institute Inc. of Cary, North Carolina.

Machine-learning models can be constructed through an at least partially automated (e.g., with little or no human involvement) process called training. During training, input data can be iteratively supplied to a machine-learning model to enable the machine-learning model to identify patterns related to the input data or to identify relationships between the input data and output data. With training, the machine-learning model can be transformed from an untrained state to a trained state. Input data can be split into one or more training sets and one or more validation sets, and the training process may be repeated multiple times. The splitting may follow a k-fold cross-validation rule, a leave-one-out-rule, a leave-p-out rule, or a holdout rule. An overview of training and using a machine-learning model is described below with respect to the flow chart of FIG. 11.

In block 1102, training data is received. In some examples, the training data is received from a remote database or a local database, constructed from various subsets of data, or input by a user. The training data can be used in its raw form for training a machine-learning model or pre-processed into another form, which can then be used for training the machine-learning model. For example, the raw form of the training data can be smoothed, truncated, aggregated, clustered, or otherwise manipulated into another form, which can then be used for training the machine-learning model.

In block 1104, a machine-learning model is trained using the training data. The machine-learning model can be trained in a supervised, unsupervised, or semi-supervised manner. In supervised training, each input in the training data is correlated to a desired output. This desired output may be a scalar, a vector, or a different type of data structure such as text or an image. This may enable the machine-learning model to learn a mapping between the inputs and desired outputs. In unsupervised training, the training data includes inputs, but not desired outputs, so that the machine-learning model has to find structure in the inputs on its own. In semi-supervised training, only some of the inputs in the training data are correlated to desired outputs.

In block 1106, the machine-learning model is evaluated. For example, an evaluation dataset can be obtained, for example, via user input or from a database. The evaluation dataset can include inputs correlated to desired outputs. The inputs can be provided to the machine-learning model and the outputs from the machine-learning model can be compared to the desired outputs. If the outputs from the machine-learning model closely correspond with the desired outputs, the machine-learning model may have a high degree of accuracy. For example, if 90% or more of the outputs from the machine-learning model are the same as the desired outputs in the evaluation dataset, the machine-learning model may have a high degree of accuracy. Otherwise, the machine-learning model may have a low degree of accuracy. The 90% number is an example only. A realistic and desirable accuracy percentage is dependent on the problem and the data.

In some examples, if, at block 1108, the machine-learning model has an inadequate degree of accuracy for a particular task, the process can return to block 1104, where the machine-learning model can be further trained using additional training data or otherwise modified to improve accuracy. However, if, at block 1108, the machine-learning model has an adequate degree of accuracy for the particular task, the process can continue to block 1110.

In block 1110, new data is received. In some examples, the new data is received from a remote database or a local database, constructed from various subsets of data, or input by a user. The new data may be unknown to the machine-learning model. For example, the machine-learning model may not have previously processed or analyzed the new data.

In block 1112, the trained machine-learning model is used to analyze the new data and provide a result. For example, the new data can be provided as input to the trained machine-learning model. The trained machine-learning model can analyze the new data and provide a result that includes a classification of the new data into a particular class, a clustering of the new data into a particular group, a prediction based on the new data, or any combination of these.

In block 1114, the result is post-processed. For example, the result can be added to, multiplied with, or otherwise combined with other data as part of a job. As another example, the result can be transformed from a first format, such as a time series format, into another format, such as a count series format. Any number and combination of operations can be performed on the result during post-processing.

Figure 12:
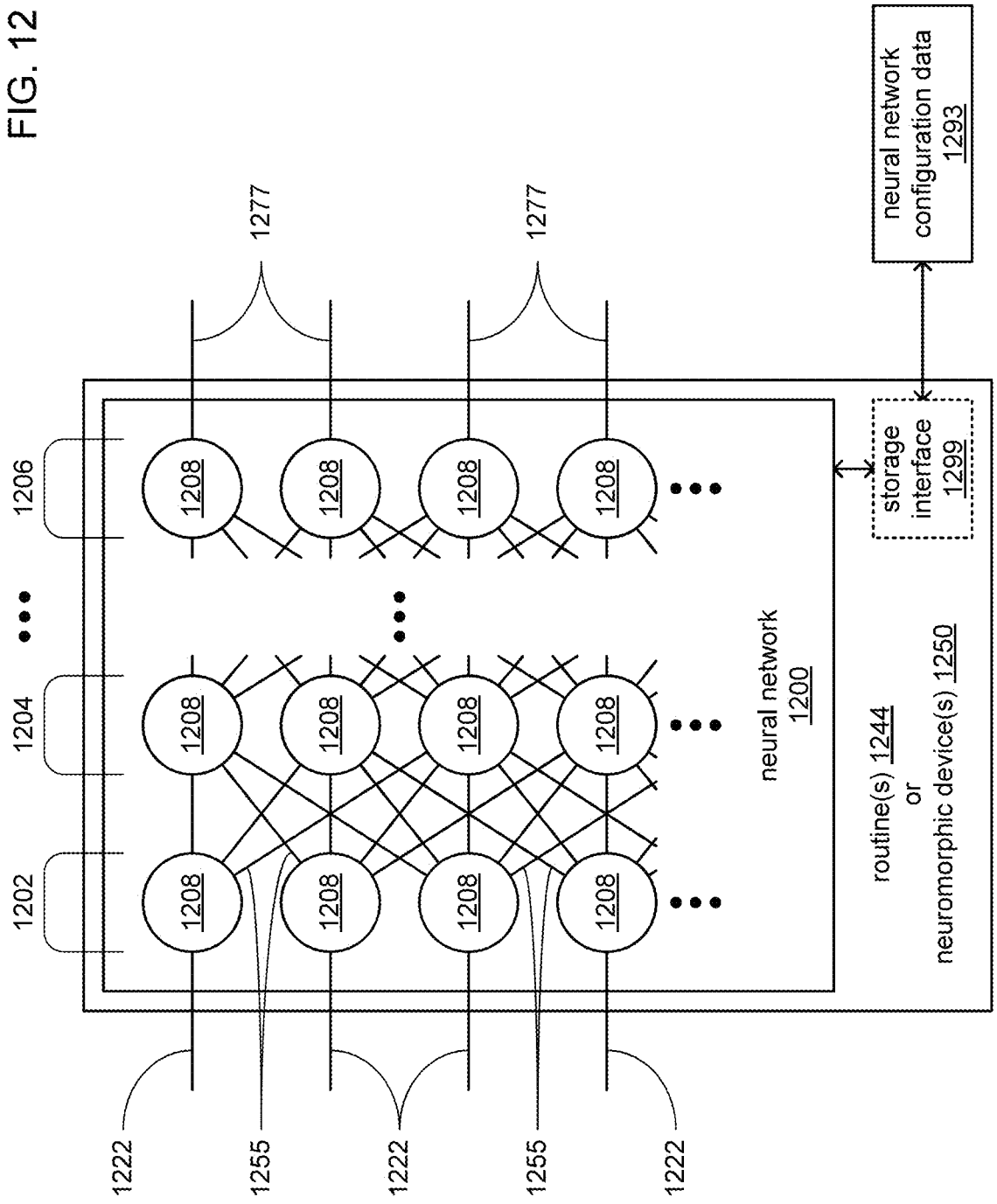
FIG. 12 shows a node-link diagram of an example of a neural network according to some aspects of the present disclosure.

A more specific example of a machine-learning model is the neural network 1200 shown in FIG. 12. The neural network 1200 is represented as multiple layers of neurons 1208 that can exchange data between one another via connections 1255 that may be selectively instantiated thereamong. The layers include an input layer 1202 for receiving input data provided at inputs 1222, one or more hidden layers 1204, and an output layer 1206 for providing a result at outputs 1277. The hidden layer(s) 1204 are referred to as hidden because they may not be directly observable or have their inputs or outputs directly accessible during the normal functioning of the neural network 1200. Although the neural network 1200 is shown as having a specific number of layers and neurons for exemplary purposes, the neural network 1200 can have any number and combination of layers, and each layer can have any number and combination of neurons.

The neurons 1208 and connections 1255 thereamong may have numeric weights, which can be tuned during training of the neural network 1200. For example, training data can be provided to at least the inputs 1222 to the input layer 1202 of the neural network 1200, and the neural network 1200 can use the training data to tune one or more numeric weights of the neural network 1200. In some examples, the neural network 1200 can be trained using backpropagation. Backpropagation can include determining a gradient of a particular numeric weight based on a difference between an actual output of the neural network 1200 at the outputs 1277 and a desired output of the neural network 1200. Based on the gradient, one or more numeric weights of the neural network 1200 can be updated to reduce the difference therebetween, thereby increasing the accuracy of the neural network 1200. This process can be repeated multiple times to train the neural network 1200. For example, this process can be repeated hundreds or thousands of times to train the neural network 1200.

In some examples, the neural network 1200 is a feed-forward neural network. In a feed-forward neural network, the connections 1255 are instantiated and/or weighted so that every neuron 1208 only propagates an output value to a subsequent layer of the neural network 1200. For example, data may only move one direction (forward) from one neuron 1208 to the next neuron 1208 in a feed-forward neural network. Such a "forward" direction may be defined as proceeding from the input layer 1202 through the one or more hidden layers 1204, and toward the output layer 1206.

In other examples, the neural network 1200 may be a recurrent neural network. A recurrent neural network can include one or more feedback loops among the connections 1255, thereby allowing data to propagate in both forward and backward through the neural network 1200. Such a "backward" direction may be defined as proceeding in the opposite direction of forward, such as from the output layer 1206 through the one or more hidden layers 1204, and toward the input layer 1202. This can allow for information to persist within the recurrent neural network. For example, a recurrent neural network can determine an output based at least partially on information that the recurrent neural network has seen before, giving the recurrent neural network the ability to use previous input to inform the output.

In some examples, the neural network 1200 operates by receiving a vector of numbers from one layer; transforming the vector of numbers into a new vector of numbers using a matrix of numeric weights, a nonlinearity, or both; and providing the new vector of numbers to a subsequent layer ("subsequent" in the sense of moving "forward") of the neural network 1200. Each subsequent layer of the neural network 1200 can repeat this process until the neural network 1200 outputs a final result at the outputs 1277 of the output layer 1206. For example, the neural network 1200 can receive a vector of numbers at the inputs 1222 of the input layer 1202. The neural network 1200 can multiply the vector of numbers by a matrix of numeric weights to determine a weighted vector. The matrix of numeric weights can be tuned during the training of the neural network 1200. The neural network 1200 can transform the weighted vector using a nonlinearity, such as a sigmoid tangent or the hyperbolic tangent. In some examples, the non linearity can include a rectified linear unit, which can be expressed using the equation $y=\max(x, 0)$ where y is the output and x is an input value from the weighted vector. The transformed output can be supplied to a subsequent layer (e.g., a hidden layer 1204) of the neural network 1200. The subsequent layer of the neural network 1200 can receive the transformed output, multiply the transformed output by a matrix of numeric weights and a nonlinearity, and provide the result to yet another layer of the neural network 1200 (e.g., another, subsequent, hidden layer 1204). This process continues until the neural network 1200 outputs a final result at the outputs 1277 of the output layer 1206.

As also depicted in FIG. 12, the neural network 1200 may be implemented either through the execution of the instructions of one or more routines 1244 by central processing units (CPUs), or through the use of one or more neuromorphic devices 1250 that incorporate a set of memristors (or other similar components) that each function to implement one of the neurons 1208 in hardware. Where multiple neuromorphic devices 1250 are used, they may be interconnected in a depth-wise manner to enable implementing neural networks with greater quantities of layers, and/or in a width-wise manner to enable implementing neural networks having greater quantities of neurons 1208 per layer.

The neuromorphic device 1250 may incorporate a storage interface 1299 by which neural network configuration data 1293 that is descriptive of various parameters and hyperparameters of the neural network 1200 may be stored and/or retrieved. More specifically, the neural network configuration data 1293 may include such parameters as weighting and/or biasing values derived through the training of the neural network 1200, as has been described. Alternatively or additionally, the neural network configuration data 1293 may include such hyperparameters as the manner in which the neurons 1208 are to be interconnected (e.g., feed-forward or recurrent), the trigger function to be implemented within the neurons 1208, the quantity of layers and/or the overall quantity of the neurons 1208. The neural network configuration data 1293 may provide such information for more than one neuromorphic device 1250 where multiple ones have been interconnected to support larger neural networks.

Other examples of the present disclosure may include any number and combination of machine-learning models having any number and combination of characteristics. The machine-learning model(s) can be trained in a supervised, semi-supervised, or unsupervised manner, or any combination of these. The machine-learning model(s) can be implemented using a single computing device or multiple computing devices, such as the communications grid computing system 400 discussed above.

Implementing some examples of the present disclosure at least in part by using machine-learning models can reduce the total number of processing iterations, time, memory, electrical power, or any combination of these consumed by a computing device when analyzing data. For example, a neural network may more readily identify patterns in data than other approaches. This may enable the neural network to analyze the data using fewer processing cycles and less memory than other approaches, while obtaining a similar or greater level of accuracy.

Some machine-learning approaches may be more efficiently and speedily executed and processed with machine-learning specific processors (e.g., not a generic CPU). Such processors may also provide an energy savings when compared to generic CPUs. For example, some of these processors can include a graphical processing unit (GPU), an application-specific integrated circuit (ASIC), a field-programmable gate array (FPGA), an artificial intelligence (AI) accelerator, a neural computing core, a neural computing engine, a neural processing unit, a purpose-built chip architecture for deep learning, and/or some other machine-learning specific processor that implements a machine learning approach or one or more neural networks using semiconductor (e.g., silicon (Si), gallium arsenide(GaAs)) devices. These processors may also be employed in heterogeneous computing architectures with a number of and/or a variety of different types of cores, engines, nodes, and/or layers to achieve various energy efficiencies, processing speed improvements, data communication speed improvements, and/or data efficiency targets and improvements throughout various parts of the system when compared to a homogeneous computing architecture that employs CPUs for general purpose computing.

Figure 13:
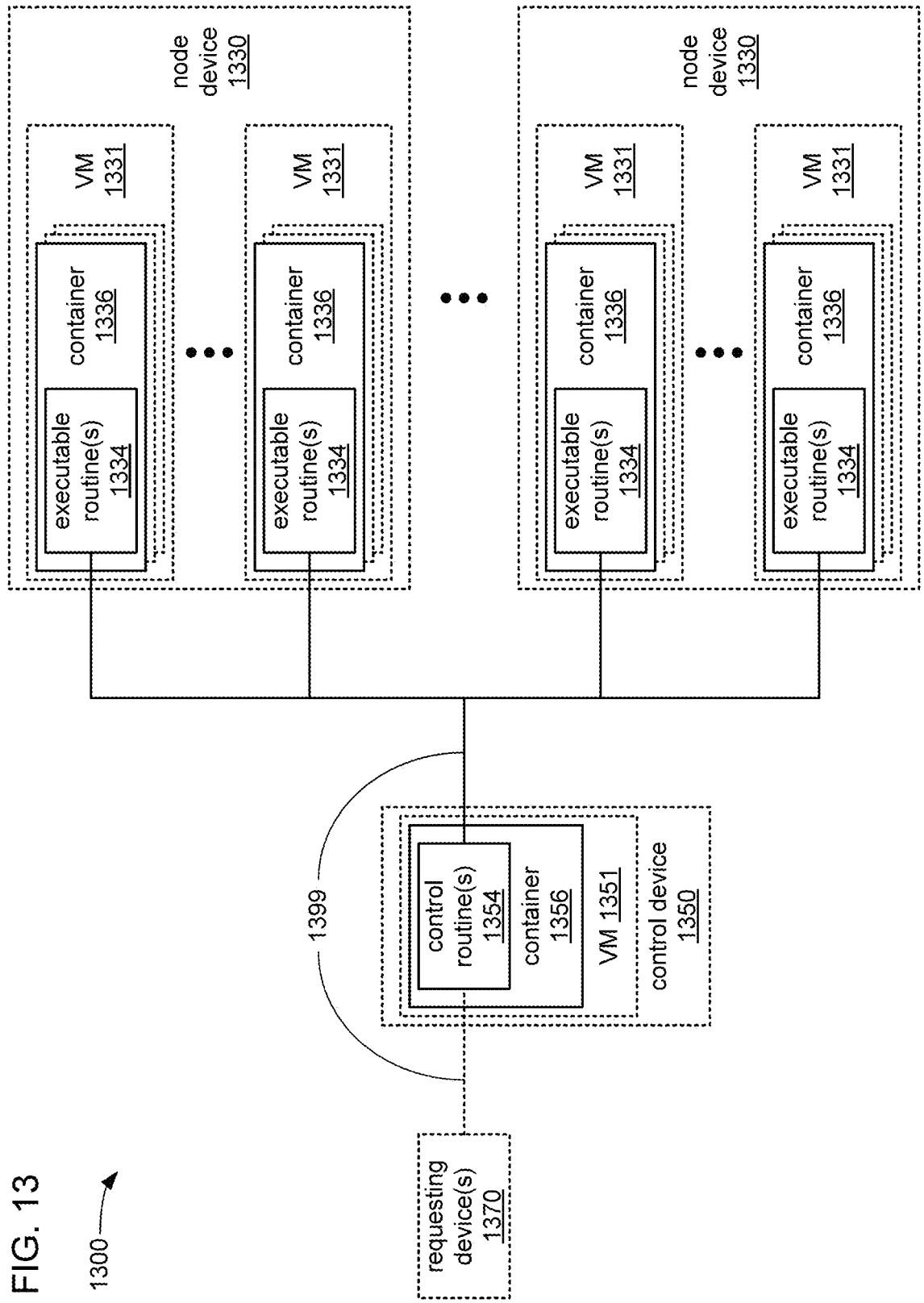
FIG. 13 shows various aspects of the use of containers as a mechanism to allocate processing, storage and/or other resources of a processing system to the performance of various analyses according to some aspects of the present disclosure.

FIG. 13 illustrates various aspects of the use of containers 1336 as a mechanism to allocate processing, storage and/or other resources of a processing system 1300 to the performance of various analyses. More specifically, in a processing system 1300 that includes one or more node devices 1330 (e.g., the aforementioned grid system 400), the processing, storage and/or other resources of each node device 1330 may be allocated through the instantiation and/or maintenance of multiple containers 1336 within the node devices 1330 to support the performance(s) of one or more analyses. As each container 1336 is instantiated, predetermined amounts of processing, storage and/or other resources may be allocated thereto as part of creating an execution environment therein in which one or more executable routines 1334 may be executed to cause the performance of part or all of each analysis that is requested to be performed.

It may be that at least a subset of the containers 1336 are each allocated a similar combination and amounts of resources so that each is of a similar configuration with a similar range of capabilities, and therefore, are interchangeable. This may be done in embodiments in which it is desired to have at least such a subset of the containers 1336 already instantiated prior to the receipt of requests to perform analyses, and thus, prior to the specific resource requirements of each of those analyses being known.

Alternatively or additionally, it may be that at least a subset of the containers 1336 are not instantiated until after the processing system 1300 receives requests to perform analyses where each request may include indications of the resources required for one of those analyses. Such information concerning resource requirements may then be used to guide the selection of resources and/or the amount of each resource allocated to each such container 1336. As a result, it may be that one or more of the containers 1336 are caused to have somewhat specialized configurations such that there may be differing types of containers to support the performance of different analyses and/or different portions of analyses.

It may be that the entirety of the logic of a requested analysis is implemented within a single executable routine 1334. In such embodiments, it may be that the entirety of that analysis is performed within a single container 1336 as that single executable routine 1334 is executed therein. However, it may be that such a single executable routine 1334, when executed, is at least intended to cause the instantiation of multiple instances of itself that are intended to be executed at least partially in parallel. This may result in the execution of multiple instances of such an executable routine 1334 within a single container 1336 and/or across multiple containers 1336.

Alternatively or additionally, it may be that the logic of a requested analysis is implemented with multiple differing executable routines 1334. In such embodiments, it may be that at least a subset of such differing executable routines 1334 are executed within a single container 1336. However, it may be that the execution of at least a subset of such differing executable routines 1334 is distributed across multiple containers 1336.

Where an executable routine 1334 of an analysis is under development, and/or is under scrutiny to confirm its functionality, it may be that the container 1336 within which that executable routine 1334 is to be executed is additionally configured assist in limiting and/or monitoring aspects of the functionality of that executable routine 1334. More specifically, the execution environment provided by such a container 1336 may be configured to enforce limitations on accesses that are allowed to be made to memory and/or I/O addresses to control what storage locations and/or I/O devices may be accessible to that executable routine 1334. Such limitations may be derived based on comments within the programming code of the executable routine 1334 and/or other information that describes what functionality the executable routine 1334 is expected to have, including what memory and/or I/O accesses are expected to be made when the executable routine 1334 is executed. Then, when the executable routine 1334 is executed within such a container 1336, the accesses that are attempted to be made by the executable routine 1334 may be monitored to identify any behavior that deviates from what is expected.

Where the possibility exists that different executable routines 1334 may be written in different programming languages, it may be that different subsets of containers 1336 are configured to support different programming languages. In such embodiments, it may be that each executable routine 1334 is analyzed to identify what programming language it is written in, and then what container 1336 is assigned to support the execution of that executable routine 1334 may be at least partially based on the identified programming language. Where the possibility exists that a single requested analysis may be based on the execution of multiple executable routines 1334 that may each be written in a different programming language, it may be that at least a subset of the containers 1336 are configured to support the performance of various data structure and/or data format conversion operations to enable a data object output by one executable routine 1334 written in one programming language to be accepted as an input to another executable routine 1334 written in another programming language.

As depicted, at least a subset of the containers 1336 may be instantiated within one or more VMs 1331 that may be instantiated within one or more node devices 1330. Thus, in some embodiments, it may be that the processing, storage and/or other resources of at least one node device 1330 may be partially allocated through the instantiation of one or more VMs 1331, and then in turn, may be further allocated within at least one VM 1331 through the instantiation of one or more containers 1336.

In some embodiments, it may be that such a nested allocation of resources may be carried out to effect an allocation of resources based on two differing criteria. By way of example, it may be that the instantiation of VMs 1331 is used to allocate the resources of a node device 1330 to multiple users or groups of users in accordance with any of a variety of service agreements by which amounts of processing, storage and/or other resources are paid for each such user or group of users. Then, within each VM 1331 or set of VMs 1331 that is allocated to a particular user or group of users, containers 1336 may be allocated to distribute the resources allocated to each VM 1331 among various analyses that are requested to be performed by that particular user or group of users.

As depicted, where the processing system 1300 includes more than one node device 1330, the processing system 1300 may also include at least one control device 1350 within which one or more control routines 1354 may be executed to control various aspects of the use of the node device(s) 1330 to perform requested analyses. By way of example, it may be that at least one control routine 1354 implements logic to control the allocation of the processing, storage and/or other resources of each node device 1330 to each VM 1331 and/or container 1336 that is instantiated therein. Thus, it may be the control device(s) 1350 that effects a nested allocation of resources, such as the aforementioned example allocation of resources based on two differing criteria.

As also depicted, the processing system 1300 may also include one or more distinct requesting devices 1370 from which requests to perform analyses may be received by the control device(s) 1350. Thus, and by way of example, it may be that at least one control routine 1354 implements logic to monitor for the receipt of requests from authorized users and/or groups of users for various analyses to be performed using the processing, storage and/or other resources of the node device(s) 1330 of the processing system 1300. The control device(s) 1350 may receive indications of the availability of resources, the status of the performances of analyses that are already underway, and/or still other status information from the node device(s) 1330 in response to polling, at a recurring interval of time, and/or in response to the occurrence of various preselected events. More specifically, the control device(s) 1350 may receive indications of status for each container 1336, each VM 1331 and/or each node device 1330. At least one control routine 1354 may implement logic that may use such information to select container(s) 1336, VM(s) 1331 and/or node device(s) 1330 that are to be used in the execution of the executable routine(s) 1334 associated with each requested analysis.

As further depicted, in some embodiments, the one or more control routines 1354 may be executed within one or more containers 1356 and/or within one or more VMs 1351 that may be instantiated within the one or more control devices 1350. It may be that multiple instances of one or more varieties of control routine 1354 may be executed within separate containers 1356, within separate VMs 1351 and/or within separate control devices 1350 to better enable parallelized control over parallel performances of requested analyses, to provide improved redundancy against failures for such control functions, and/or to separate differing ones of the control routines 1354 that perform different functions. By way of example, it may be that multiple instances of a first variety of control routine 1354 that communicate with the requesting device(s) 1370 are executed in a first set of containers 1356 instantiated within a first VM 1351, while multiple instances of a second variety of control routine 1354 that control the allocation of resources of the node device(s) 1330 are executed in a second set of containers 1356 instantiated within a second VM 1351. It may be that the control of the allocation of resources for performing requested analyses may include deriving an order of performance of portions of each requested analysis based on such factors as data dependencies thereamong, as well as allocating the use of containers 1336 in a manner that effectuates such a derived order of performance.

Where multiple instances of control routine 1354 are used to control the allocation of resources for performing requested analyses, such as the assignment of individual ones of the containers 1336 to be used in executing executable routines 1334 of each of multiple requested analyses, it may be that each requested analysis is assigned to be controlled by just one of the instances of control routine 1354. This may be done as part of treating each requested analysis as one or more "ACID transactions" that each have the four properties of atomicity, consistency, isolation and durability such that a single instance of control routine 1354 is given full control over the entirety of each such transaction to better ensure that all of each such transaction is either entirely performed or is entirely not performed. Allowing partial performances to occur may cause cache incoherencies and/or data corruption issues.

As additionally depicted, the control device(s) 1350 may communicate with the requesting device(s) 1370 and with the node device(s) 1330 through portions of a network 1399 extending thereamong. Again, such a network as the depicted network 1399 may be based on any of a variety of wired and/or wireless technologies, and may employ any of a variety of protocols by which commands, status, data and/or still other varieties of information may be exchanged. It may be that one or more instances of a control routine 1354 cause the instantiation and maintenance of a web portal or other variety of portal that is based on any of a variety of communication protocols, etc. (e.g., a restful API). Through such a portal, requests for the performance of various analyses may be received from requesting device(s) 1370, and/or the results of such requested analyses may be provided thereto. Alternatively or additionally, it may be that one or more instances of a control routine 1354 cause the instantiation of and maintenance of a message passing interface and/or message queues. Through such an interface and/or queues, individual containers 1336 may each be assigned to execute at least one executable routine 1334 associated with a requested analysis to cause the performance of at least a portion of that analysis.

Although not specifically depicted, it may be that at least one control routine 1354 may include logic to implement a form of management of the containers 1336 based on the Kubernetes container management platform promulgated by Could Native Computing Foundation of San Francisco, CA, USA. In such embodiments, containers 1336 in which executable routines 1334 of requested analyses may be instantiated within "pods" (not specifically shown) in which other containers may also be instantiated for the execution of other supporting routines. Such supporting routines may cooperate with control routine(s) 1354 to implement a communications protocol with the control device(s) 1350 via the network 1399 (e.g., a message passing interface, one or more message queues, etc.). Alternatively or additionally, such supporting routines may serve to provide access to one or more storage repositories (not specifically shown) in which at least data objects may be stored for use in performing the requested analyses.

Figure 14:
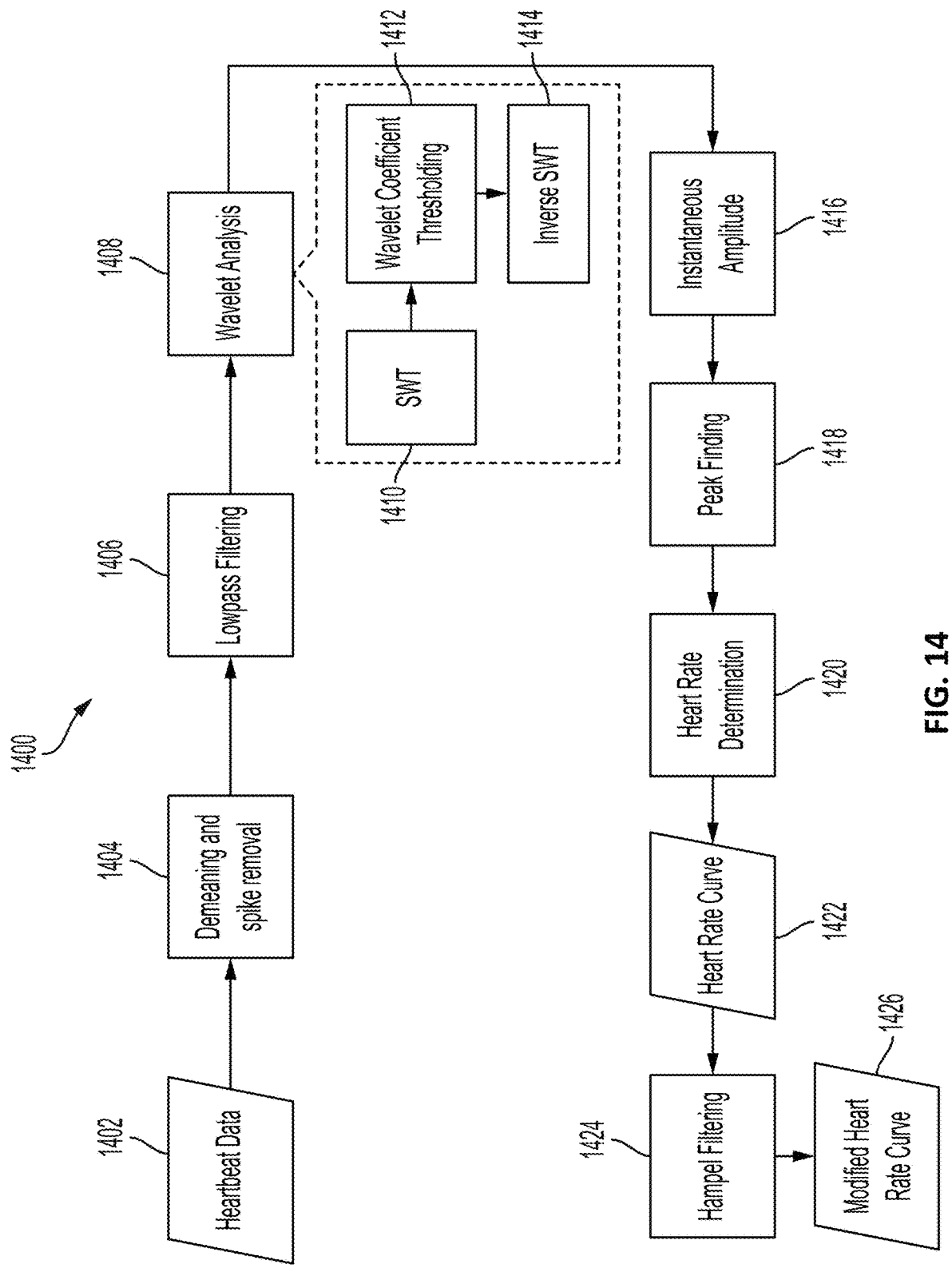
FIG. 14 shows an example of a noise-reduction process for reducing noise in heartbeat data, according to some aspects of the present disclosure.

FIG. 14 shows an example of a noise-reduction process 1400 for reducing noise in heartbeat data (e.g., ECG data) according to some aspects of the present disclosure. The noise-reduction process 1400 may be implemented by one or more processors, which may be arranged and configured in any manner described above with respect to FIGS. 1-13. In some examples, the one or more processors may be part of a wearable device, such as a smart watch, armband, bracelet, or chest band.

The noise-reduction process 1400 can begin with the one or more processors receiving heartbeat data 1402, such as an ECG signal. The heartbeat data can represent the electrical activity in the wearer's heart. The heartbeat data may be obtained using electrodes placed at certain locations on the chest, arms, and/or legs of a wearer. The heartbeat data 1402 can be received directly from the electrodes or from another source, such as from a remote device via one or more networks (e.g., a local area network or the Internet). One example of such a remote device can be a wearable heart-rate sensor that includes the electrodes.

In block 1404, the one or more processors can perform a demeaning and/or a spike-removal process on the heartbeat data 1402. For example, many ECG signals contain amplitude inconsistencies or spikes. These may be due to failure in hardware connections and can lead to false R-peak detection. To combat this problem, the one or more processors can demean the heartbeat data 1402, which can involve subtracting the mean value ($\bar{x}$) from the signal. Additionally or alternatively, the one or more processors can calculate a z-score for each point $x_t$ in the heartbeat data 1402 according to the following equation: z-score=$(x_t-\bar{x})/\sigma$, where $\sigma$ is a standard deviation of the sample of the heartbeat data. If the z-score for a given point $x_t$ meets or exceeds a predefined threshold, such as 5, the one or more processors can replace the point's value with 0.

Figure 15A:
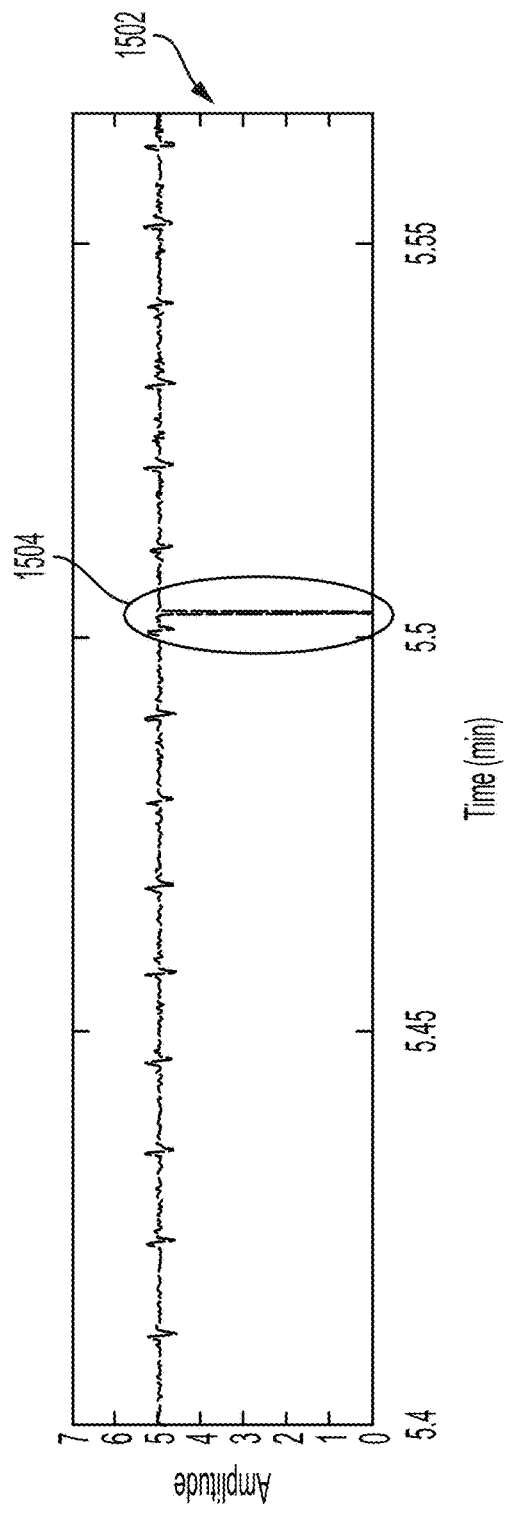
FIGS. 15A-B show graphs of examples of raw heartbeat data and demeaned heartbeat data with spikes removed, according to some aspects of the present disclosure.
Figure 15B:
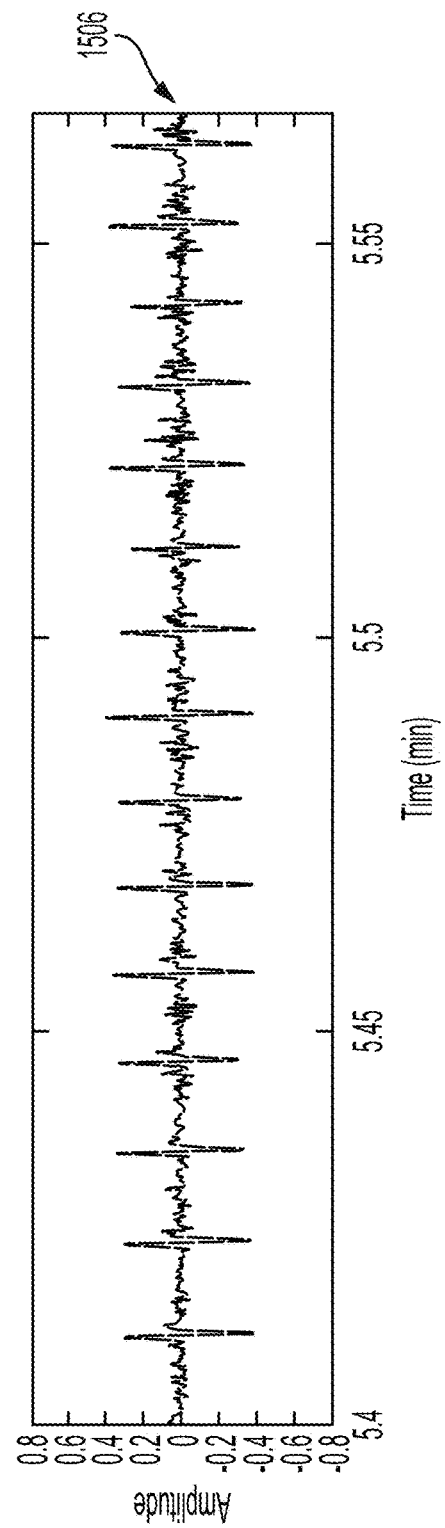

One example of the demeaning and spike removal process is shown in FIGS. 15A-B. The top graph 1502 of FIG. 15A depicts a raw ECG signal. As shown, there is a spike 1504 with an amplitude of 5. The bottom graph 1506 of FIG. 15B depicts the demeaned signal with spikes removed. By comparing the top graph 1502 to the bottom graph 1506, it can clearly be seen that the spike 1504 has been removed and the signal amplitude is now more consistently in the range of −0.4-0.4.

Continuing with FIG. 14, in block 1406, the one or more processors can perform lowpass filtering on the demeaned/de-spiked heartbeat data 1402 (from block 1404), to thereby generate a set of filtered heartbeat data. The lowpass filtering can remove high-frequency noise in the signal. In some examples, the lowpass filter can be a Butterworth filter. Other kinds of lowpass filters are also contemplated within the scope of this disclosure. The lowpass filter may be of any suitable order and may have any suitable cutoff frequency. For instance, a lowpass filter with an order of 8-11, such as an order of 10, and a cutoff frequency in the range of 15-25 Hz, such as 17.5 Hz, may be used.

Figure 16A:
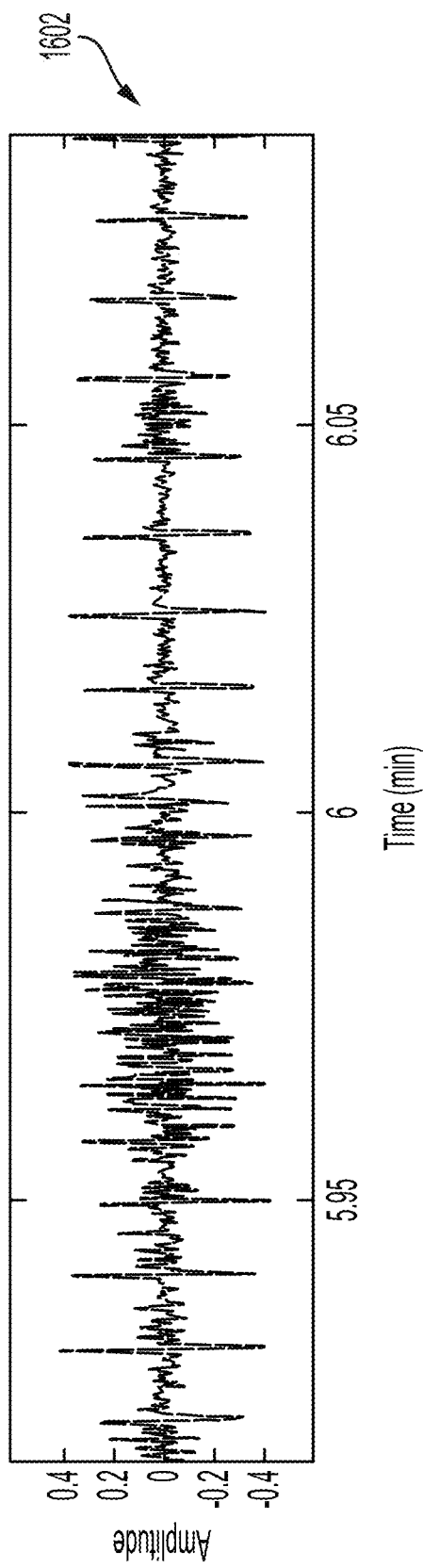
FIGS. 16A-B show graphs of examples of demeaned heartbeat data and filtered heartbeat data, according to some aspects of the present disclosure.
Figure 16B:
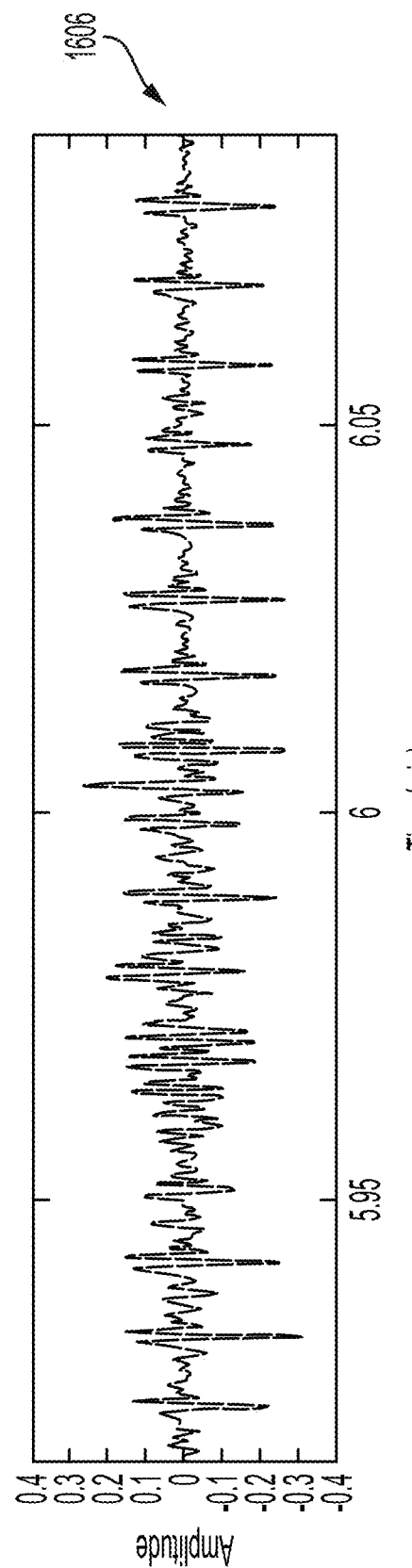

One example of the filtering process is shown in FIGS. 16A-B. The top graph 1602 of FIG. 16A depicts an ECG signal following block 1404, after it has been demeaned and spikes have been removed. The bottom graph 1606 of FIG. 16B depicts the filtered ECG signal, after a lowpass Butterworth filter has been applied.

Figure 17B:
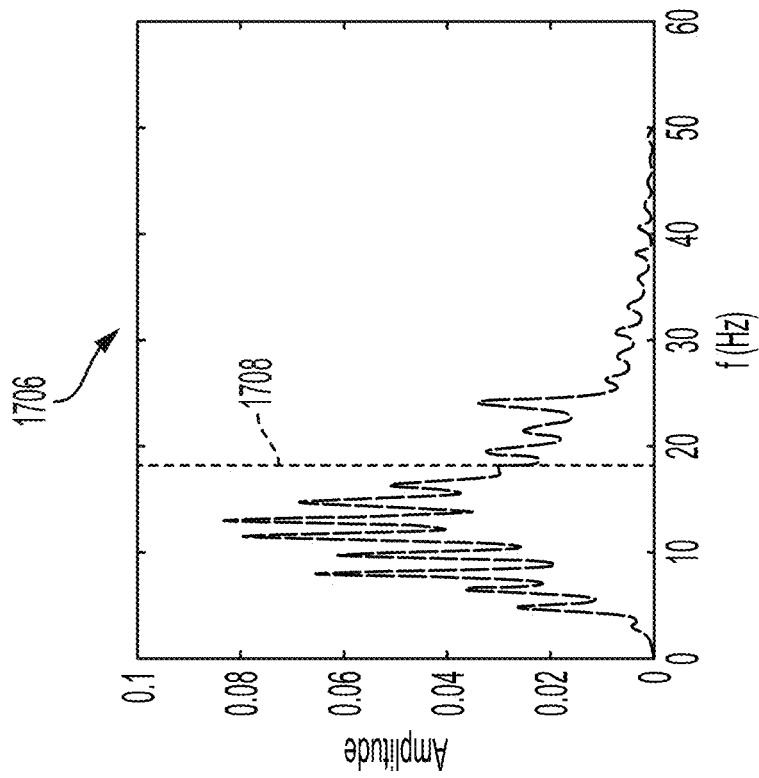
FIGS. 17A-B show graphs of examples of parametric power spectral densities, according to some aspects of the present disclosure.
Figure 17A:
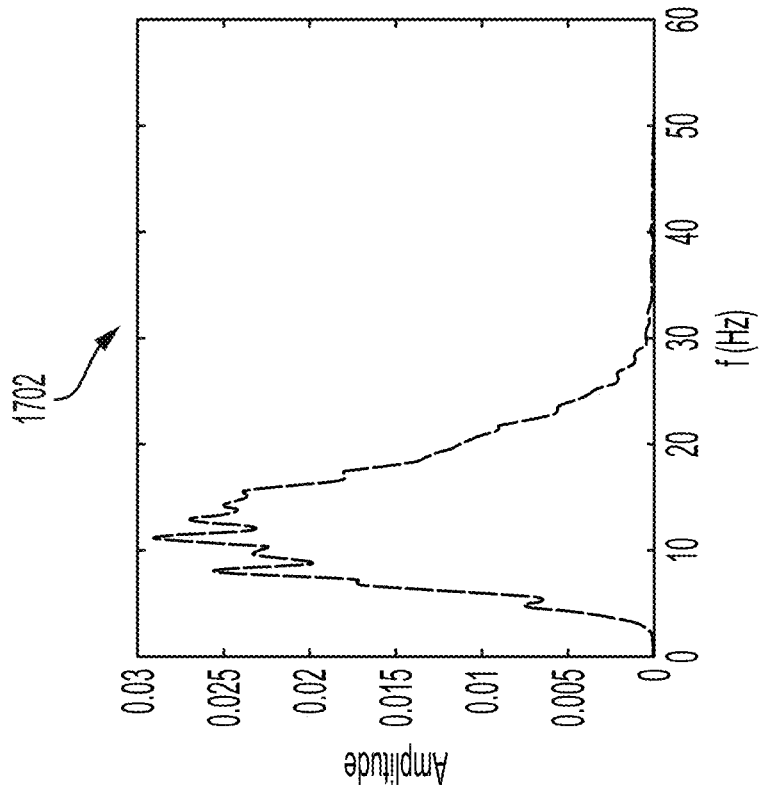

To determine a suitable frequency cutoff for the lowpass filter, in some examples a parametric power spectral density (PPSD) can be used. In particular, the one or more processors can determine a first PPSD of a first set of heartbeat data 1402 (e.g., a first ECG signal) obtained when a subject is at rest. The one or more processors can also determine a second PPSD of a second set of heartbeat data (e.g., a second ECG signal) obtained when the subject is moving, for instance when the subject is running. The one or more processors can then compare the two PPSDs to determine a suitable frequency cutoff for the low pass filter. One example of this is shown in FIGS. 17A-B. As shown, the left graph 1702 of FIG. 17A depicts a first PPSD for a 10-second segment of a first ECG signal obtained when a subject is at rest. The right graph 1706 of FIG. 17B depicts a second PPSD for a 10-second segment of a second ECG signal obtained when the subject is running. By comparing the graphs 1702, 1706, it can be seen that the right graph 1706 has frequency spikes above 17.5 Hz that do not exist in the left graph 1702, possibly due to noise introduced from the movement of the subject. To help combat such noise, a lowpass frequency cutoff of 17.5 Hz can be chosen, as represented by the line 1708.

Continuing with FIG. 14, in block 1408, the one or more processors can perform a wavelet analysis on the filtered set of heartbeat data (from block 1406). This may involve sub-steps 1410-1414. Beginning with step 1410, the one or more processors can perform a stationary wavelet transform (SWT) on the filtered set of heartbeat data. The stationary wavelet transform decomposes a time series x(t) into a set of scaled and translated wavelets. The stationary wavelet transform can be defined as follows:

$$W(a, b) = \frac{1}{\sqrt{a}} \int_{-\infty}^{\infty} \bar{\Psi} \frac{t-b}{a} x(t) dt$$

where $\bar{\psi}$ is the complex conjugate of the mother wavelet W, and a and b are the scale and shift parameters, respectively. The resulting decomposition is J levels of detail coefficients and one level of scaling coefficients, each of length N. In some examples, a SWT with J=10 levels and a Daubechies 3 mother wavelet may be used.

At step 1412, the one or more processors apply a threshold to the set of wavelet coefficients, to generate a reduced set of wavelet coefficients. In some examples, the threshold may be determined according to the following equation:

$$\lambda = \sigma\sqrt{2\log N}$$

where $\sigma$ can be computed as median $|d_1|/0.6745$, where $d_1$ is a subset of the detail coefficients, such as the detail coefficients at the first level. Wavelet coefficients that meet or exceed the threshold can be set to zero. Using this approach, the last seven or eight levels of detail coefficients, which we expect to contain the motion artifacts, may be set to zero. This can assist in denoising the signal and removing the motion artifacts.

Figure 18A:
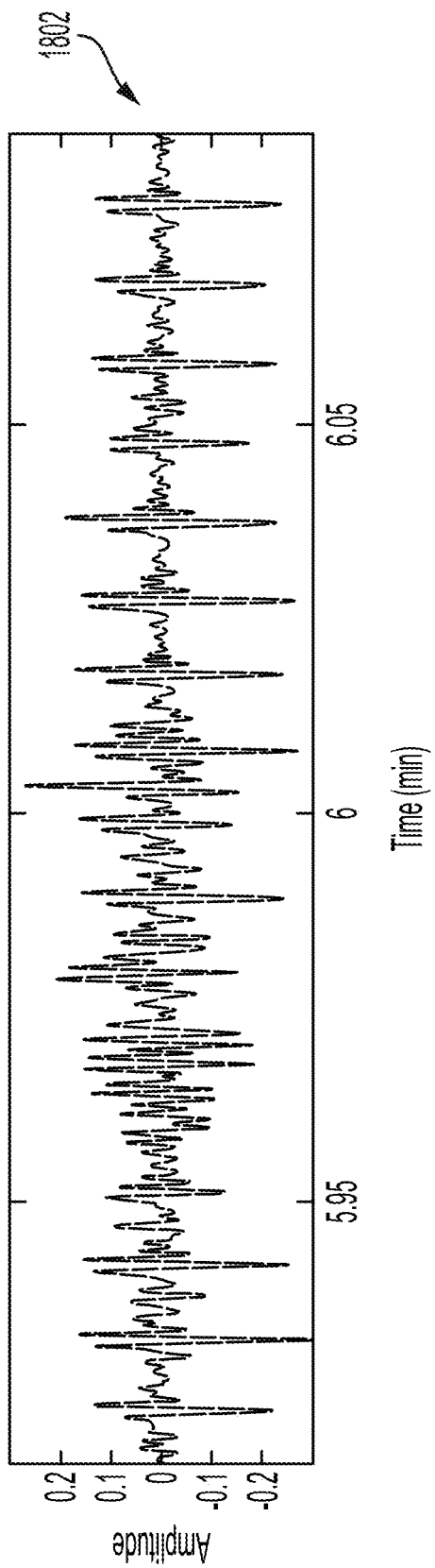
FIGS. 18A-B show graphs of examples of heartbeat data after lowpass filtering and heartbeat data after stationary wavelet analysis, according to some aspects of the present disclosure.
Figure 18B:
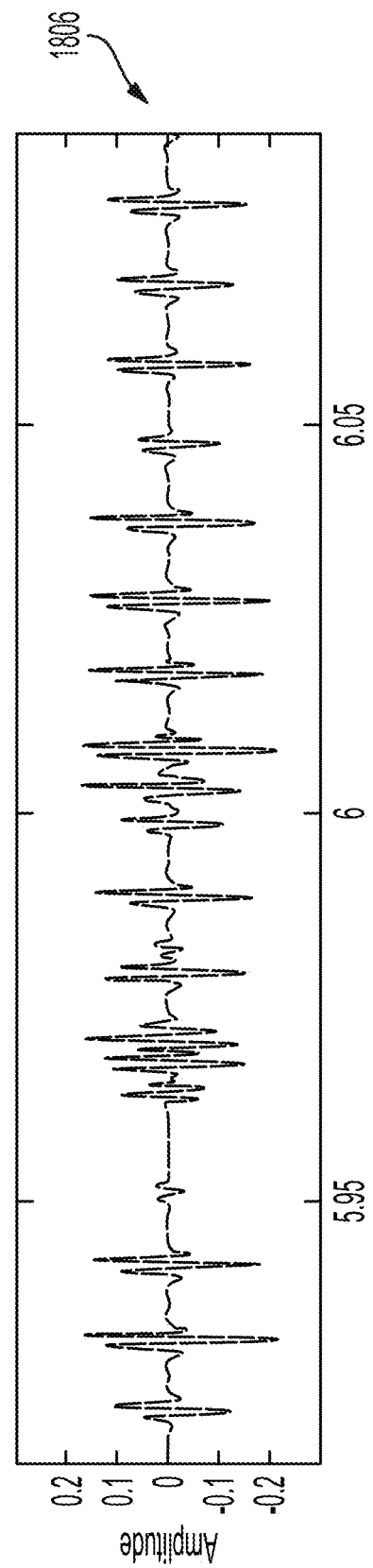

At step 1414, the one or more processors generates an inverse wavelet signal by applying an inverse wavelet transform (IWT) to the reduced set of wavelet coefficients (from step 1412). The inverse wavelet transform can be an inverse stationary wavelet transform. Performing the IWT can yield an inverse wavelet signal that only contains the segments of interest (e.g., the QRS complexes), with all other noise between heartbeats removed. One example of the wavelet analysis results is shown in FIGS. 18A-B. The top graph 1802 of FIG. 18A depicts the ECG signal after lowpass filtering, and the bottom graph 1806 of FIG. 18B depicts the inverse wavelet signal following wavelet analysis. By comparing these two graphs 1802, 1806, it is apparent that the bottom graph 1806 has significantly less noise, particularly between the QRS complexes, which allows the QRS complexes to be more readily identified.

Continuing with FIG. 14, in block 1416, the one or more processors can determine the instantaneous amplitudes of the data points in the inverse wavelet signal. In particular, after the wavelet analysis, each heartbeat in the ECG signal contains three peaks: two positive peaks and one negative peak. If a peak-finding method is applied at this stage, it may produce inaccurate results because only one of the three peaks is the true R-peak of interest. The other two peaks correspond to the P and T waves. To help resolve this issue, the one or more processors can compute the instantaneous amplitudes of the inverse wavelet signal. The instantaneous amplitude of a data point at time t can be defined as follows:

$$A(t)=|x(t)+iH\{x(t)\}|$$

where $H\{x(t)\}$ is the Hilbert transform of the signal $x(t)$, and i is an imaginary number defined as $\sqrt{-1}$. In other words, for each data point $x(t)$, the one or more processors may first determine a transformed amplitude value ($H\{x(t)\}$) by applying the Hilbert transform to the data point. The instantaneous amplitude for the data point can then be determined by computing an absolute value of a sum of (i) the data point, and (ii) the transformed value associated with the data point. The instantaneous amplitudes capture the envelope of the signal and the center of energy of each heartbeat, which corresponds to the R-peaks.

In block 1418, the one or more processors applies a peak-finding method to the instantaneous amplitudes (from block 1416) to identify the R-peaks. In general, peak finding methods identify local maxima in a signal. A peak can be a data point whose amplitude is greater than the amplitude of its surrounding neighbors. The peak-finding method can be configured with any suitable minimum distance between peaks, such as a minimum distance of 45 observations (e.g., 0.45 seconds) between peaks. This may further help to eliminate noise. The peak-finding method can also be configured with any suitable minimum amplitude for the peaks, such as a minimum amplitude of 0.04. Peaks below that minimum may be ignored. This may help reduce false positives.

Figure 19A:
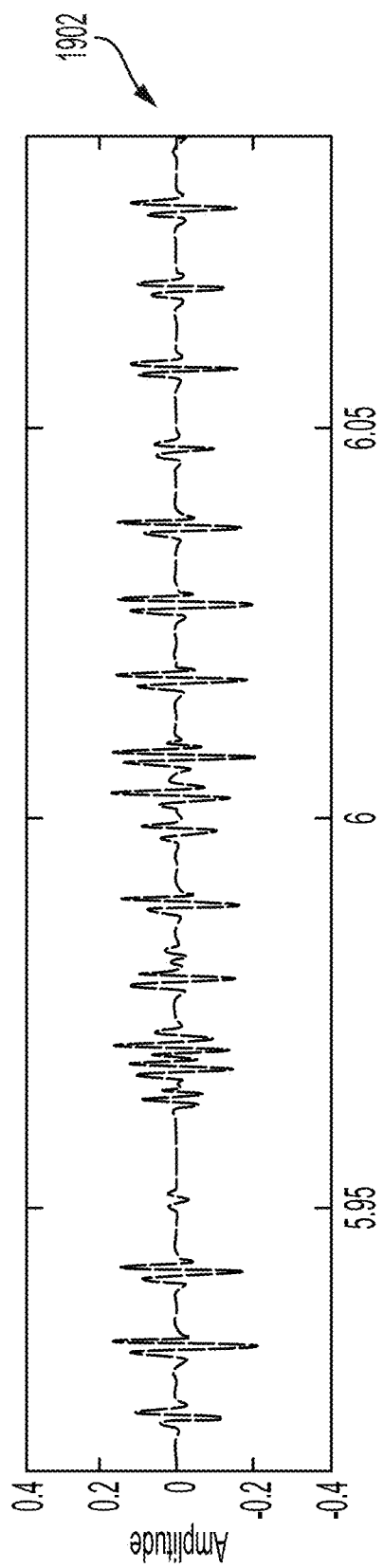
FIGS. 19A-B show graphs of examples of heartbeat data after stationary wavelet analysis and instantaneous amplitude with peaks detected, according to some aspects of the present disclosure.
Figure 19B:
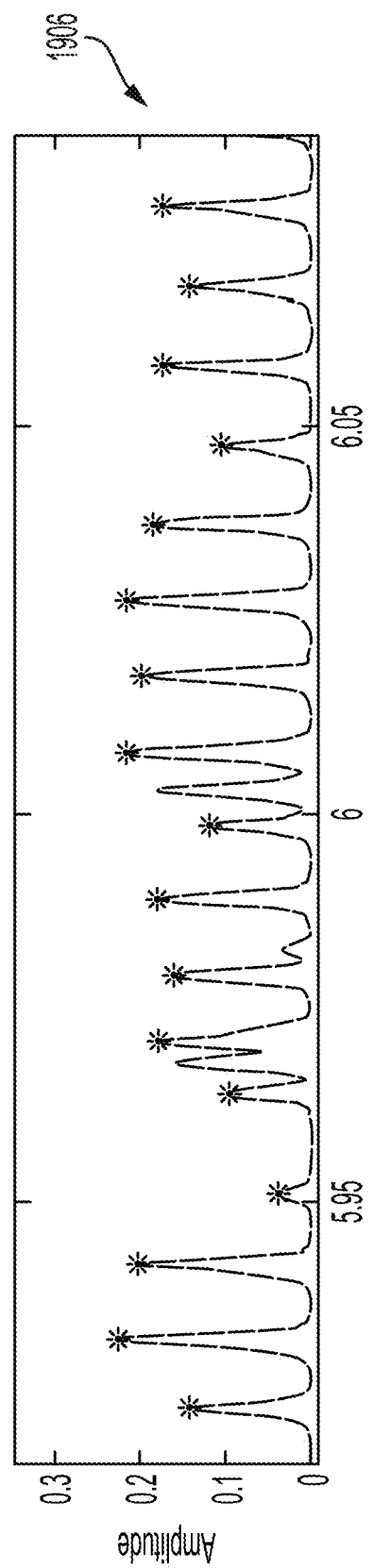

One example of the results of the peak-finding method is shown in FIGS. 19A-B. The top graph 1902 of FIG. 19A depicts the ECG signal after wavelet analysis (e.g., following block 1408), and the bottom graph 1906 of FIG. 19B shows the instantaneous amplitude of the signal with the identified peaks marked by stars. As a result of the instantaneous amplitude process, the ECG signal in the bottom graph 1906 may only contain the positive R-peaks (and thus may excludes the P and T waves) in each heartbeat.

In block 1420, the one or more processors determines a group of heart rates that collectively form a heart rate curve 1422 based on the set of R-peaks. For example, a heart rate of the wearer can be computed as the inverse of the distance between a successive pair of R-peaks (in the set of R-peaks) multiplied by the sampling frequency. This can be repeated for each successive pair of R-peaks in the set of R-peaks to generate a heart rate curve indicating the heart rates of the wearer over a time window. Each data point in the heart rate curve can represent an individual heart rate of the wearer at a given point of time during the time window.

Figure 20:
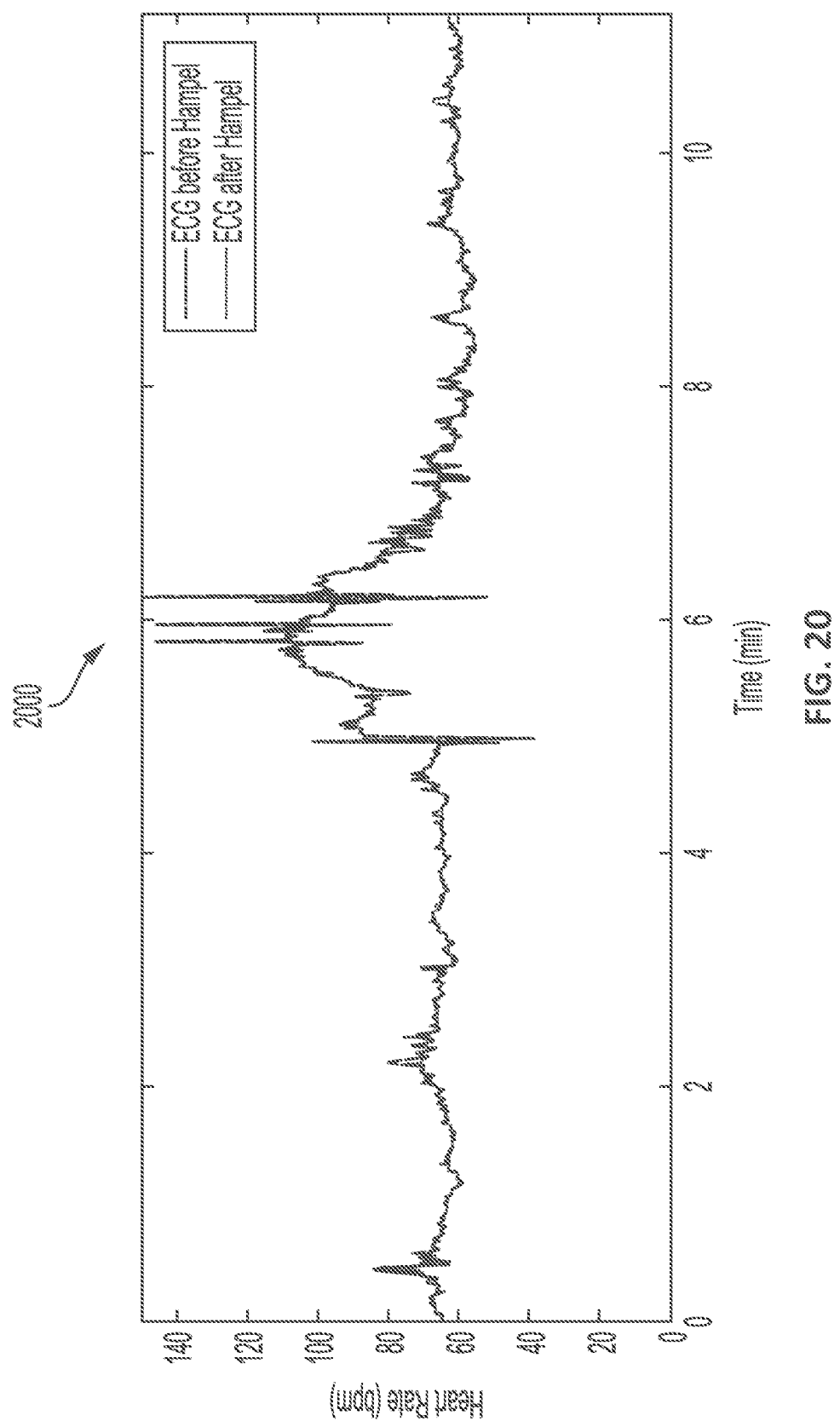
FIG. 20 shows graphs of examples of heart rates before and after Hampel filtering is applied, according to some aspects of the present disclosure.

In block 1424, the one or more processors perform Hampel filtering on the heart rate curve 1422 to generate a modified heart rate curve 1426. For example, because some R-peaks may have been missed during the previous steps, which may lead to errors in the heart rate curve 1422, the one or more processors can apply the Hampel filter to smooth out the heart rate curve 1422. The Hampel filter can identify outliers $x_t$ if:

$$|x_t - M_t| \geq 1.4826 h \times MAD$$

where $x_t$ is the signal amplitude at time t, $M_t$ is the median of $2k+1$ size window centered around $x_t$, MAD is the median absolute deviation from the median, and h is a user specified number of deviations. If $x_t$ is considered an outlier, the one or more processor can replace its value with the median of the window $M_t$. As one particular example, by using a window with a length of 10 seconds (k=500 observations) and h=2, amplitude inconsistencies can be removed. One example of this is shown in graph 2000 of FIG. 20, which shows that the heart rate curve 1422 before the Hampel filtering may still contain spikes and other outliers. These outliers are smoothed by the Hampel filtering, thereby producing a more accurate version of the heart rate curve. The heart rate curve, or a heart rate therein, may then be output to the wearer or another entity (e.g., user or device).

Figure 21A:
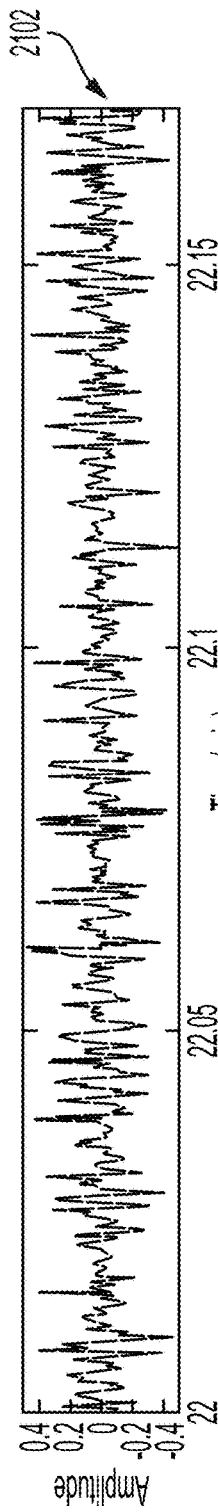
FIGS. 21A-D show graphs of examples of demeaned heartbeat data, heartbeat data after lowpass filtering, heartbeat data after wavelet analysis, and instantaneous amplitudes, according to some aspects of the present disclosure.
Figure 21B:
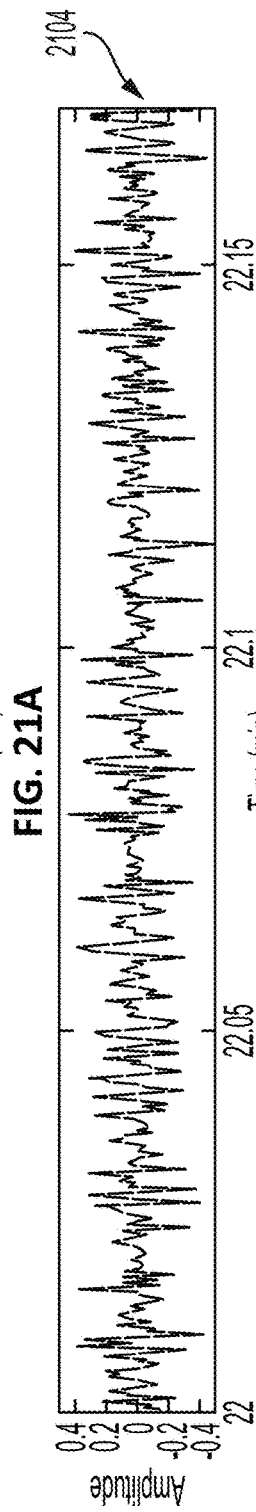
Figure 21C:
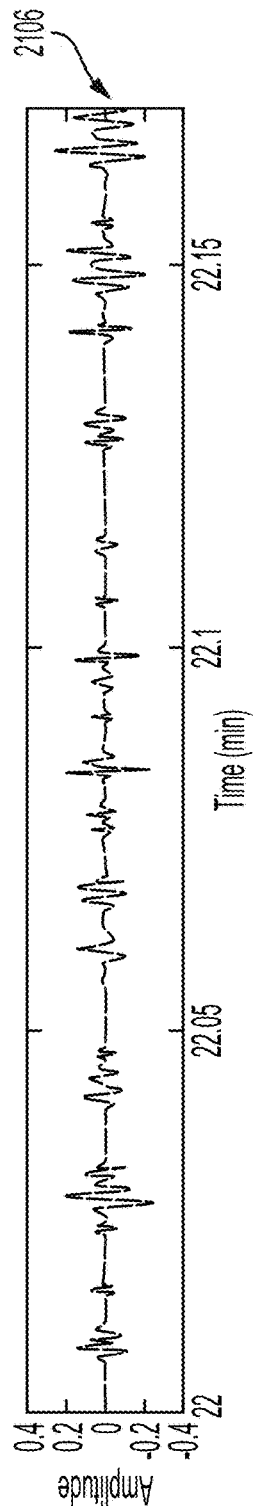
Figure 21D:
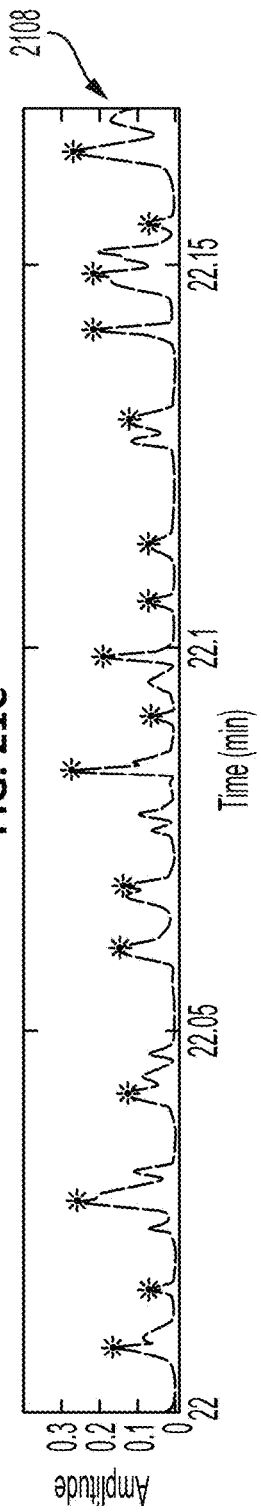

Using the techniques described above, the noise-reduction process described herein can reliably remove high-frequency motion artifacts from heartbeat data 1402. The techniques described above can also be used to detect R-peaks in heartbeat data 1402 that contains a lot of dispersed low-frequency noise. This is a common problem with wearable devices, likely caused by the motion of the electrodes against the skin, which produces high levels of noise that are difficult to analyze. For example, referring now to FIGS. 21A-D, the first graph 2102 of FIG. 21A shows the noisy original demeaned signal, and the second graph 2104 of FIG. 21B shows the heartbeat data after the lowpass filter is applied. Note that in this case, the lowpass filter did not remove much of the noise. This is because the noise is dispersed throughout the signal and is not high-frequency noise, in contrast with the motion artifacts in FIG. 16. Nevertheless, the third graph 2106 of FIG. 21C shows the result of the wavelet analysis, which is able to remove much of the remaining noise. However, many heartbeats are lost. The fourth graph 2108 of FIG. 21D shows the instantaneous amplitude as well as the peaks from the peak-finding method.

Figure 22A:
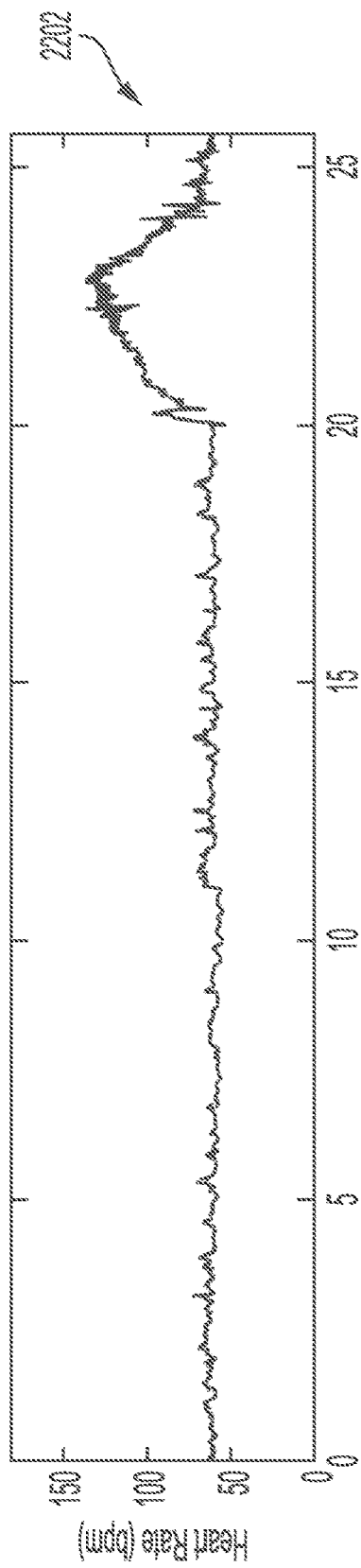
FIGS. 22A-B show graphs of examples of heart rate comparisons between the techniques described herein and a BIOPAC machine, according to some aspects of the present disclosure.
Figure 22B:
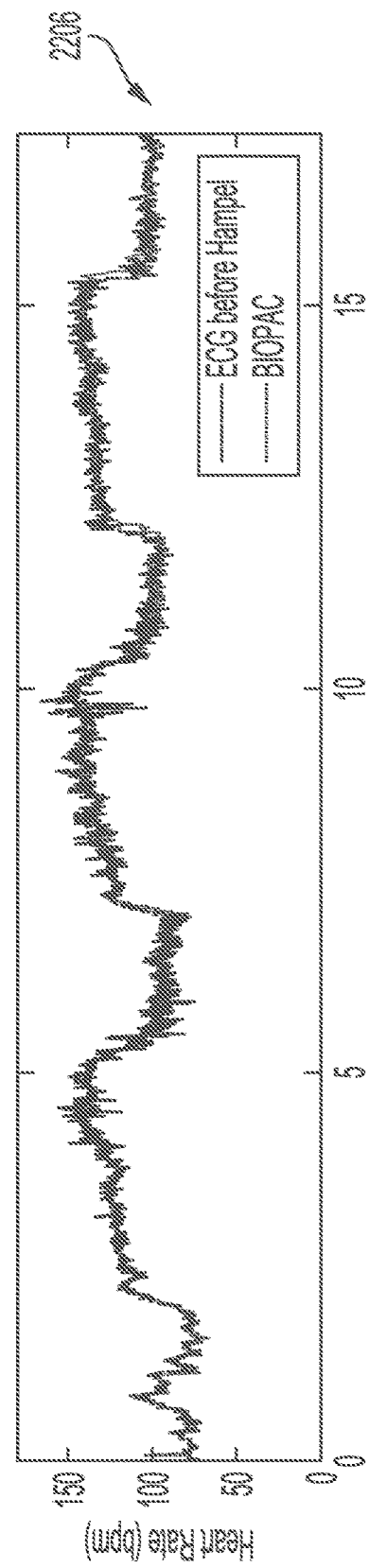

In the example of FIGS. 21A-D, although many heartbeats are lost in the wavelet analysis, the system is still able to determine the heart rate with a high degree of accuracy. For example, referring now to FIGS. 22A-B, graphs 2202, 2206 show the heart rates of two subjects performing two activity protocols, respectively. In particular, graph 2202 of FIG. 22A shows the heart rate of a first subject performing a first activity protocol, and graph 2206 of FIG. 22B shows the heart rate of a second subject performing a second activity protocol. The graphs 2202, 2206 each show a comparison of a first heart rate determined using the techniques described herein against a second heart rate determined using a BIOPAC MP160 machine, which served as a gold standard reference in the experiment. Despite the loss of some heartbeats after the wavelet analysis and thresholding, the first heart rate still very closely matches the ground truth (the second heart rate), indicating a high degree of accuracy, regardless of the activity protocol and subject.

Figure 23:
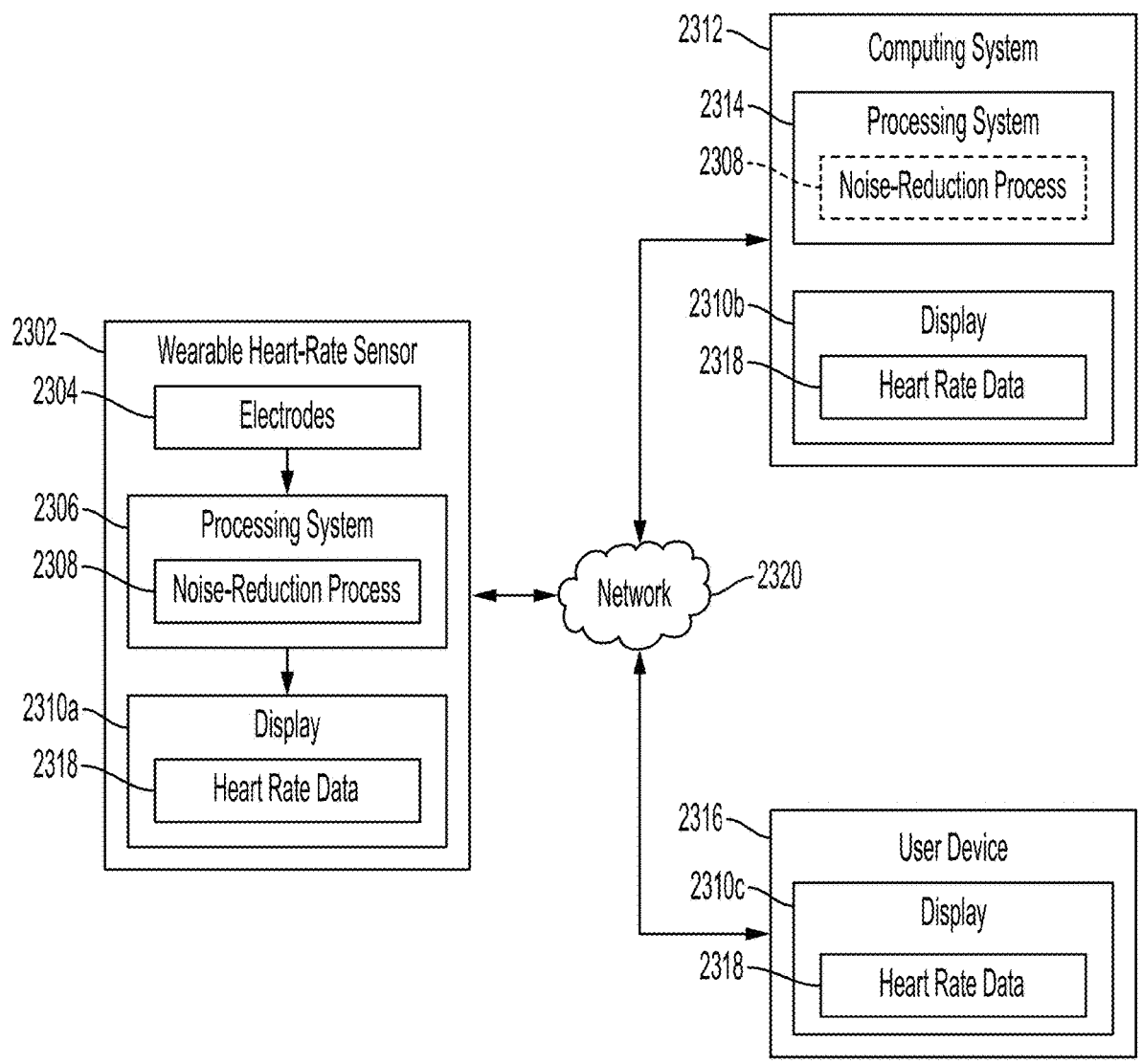
FIG. 23 shows an example of a system involving a wearable heart-rate sensor, according to some aspects of the present disclosure.

FIG. 23 shows a block diagram of an example of a system 2300 according to some aspects of the present disclosure. The system 2300 includes a wearable heart-rate sensor 2302. The wearable heart-rate sensor 2302 may be a standalone sensor device, which can have heart rate sensing as its primary functionality. Alternatively, the wearable heart-rate sensor 2302 may be included in a wearable device (e.g., a smart watch) that has additional functionality, in which case heart rate sensing may be a secondary or optional feature of the wearable device.

The wearable heart-rate sensor 2302 can include a set of electrodes 2304 positioned to be pressed against the wearer's skin. The set of electrodes 2304 can include any number of electrodes, such as 1, 2, 3, 4, or 5 electrodes. The electrodes 2304 can generate heartbeat data (e.g., an ECG signal) based on the electrical activity in the wearer's heat and transmit the heartbeat data to a processing system 2306, which includes one or more processors. In some examples, the processing system 2306 may be configured to perform the noise-reduction process 2308 described above with respect to FIG. 14 on the heartbeat data to determine heart rate data 2318 associated with the wearer. The noise-reduction process 2308 may be particularly useful when the wearer is in motion to eliminate motion artifacts and other related noise. After determining the heart rate data 2318 of the wearer, the wearable heart-rate sensor 2302 may output the heart rate data 2318 on a display 2310a, such as a liquid crystal display (LCD) or a light-emitting diode (LED) display.

In some examples, the wearable heart-rate sensor 2302 may additionally or alternatively output (e.g., transmit) the heartbeat data and/or the heart rate data 2318 to one or more other entities, such as computing system 2312 and user device 2316, for storage, analysis, and/or display. The wearable heart-rate sensor 2302 can communicate with the other entities via a wired or wireless interface. For example, the wearable heart-rate sensor 2302 may communicate with the computing system 2312 and the user device 2316 via 802.11 connections and/or Bluetooth connections. In some examples, the wearable heart-rate sensor 2302 can communicate with the other entities via one or more networks 2320, such as a local area network or the Internet.

In some examples, the computing system 2312 may receive the heartbeat data and perform the noise-reduction process 2308 using a processing system 2314, which may include any number and arrangement of processors. This may offload some of the processing from the wearable heart-rate sensor 2302 to the computing system 2312, which may be beneficial if the wearable heart-rate sensor 2302 has limited computing power or if it would otherwise be desirable to reduce the resource consumption of the wearable heart-rate sensor 2302. After performing the noise-reduction process 2308 and determining the heart rate data 2318 of the wearer, the computing system 2312 may output the heart rate data 2318 (e.g., a heart rate or a heart rate curve). For example, the computing system 2312 may output the heart rate data 2318 on its own display 2310b to a user, such as a physician monitoring the wearer's heart rate. Additionally or alternatively, the computing system 2312 may output (e.g., transmit) the heart rate data 2318 to the wearable heart-rate sensor 2302, which can output the heart rate data 2318 on its display 2310a. This may allow the wearer of the wearable heart-rate sensor 2302 to monitor their heart rate. Additionally or alternatively, the computing system 2312 may output the heart rate data 2318 to a user device 2316 that is separate from the wearable heart-rate sensor 2302 and the computing system 2312. The user device 2316 can output the heart rate data 2318 on its display 2310c. The user device 2316 correspond to a friend, family member, healthcare provider, insurer, or any other entity that is different from the wearer of the wearable heart-rate sensor 2302. This may allow another individual to remotely monitor the wearer's heart rate.

In the previous description, for the purposes of explanation, specific details are set forth in order to provide a thorough understanding of examples of the technology. But various examples can be practiced without these specific details. The figures and description are not intended to be restrictive.

The previous description provides examples that are not intended to limit the scope, applicability, or configuration of the disclosure. Rather, the previous description of the examples provides those skilled in the art with an enabling description for implementing an example. Various changes may be made in the function and arrangement of elements without departing from the spirit and scope of the technology as set forth in the appended claims.

Specific details are given in the previous description to provide a thorough understanding of the examples. But the examples may be practiced without these specific details. For example, circuits, systems, networks, processes, and other components can be shown as components in block diagram form to prevent obscuring the examples in unnecessary detail. In other examples, well-known circuits, processes, algorithms, structures, and techniques may be shown without unnecessary detail in order to avoid obscuring the examples.

Also, individual examples may have been described as a process that is depicted as a flowchart, a flow diagram, a data flow diagram, a structure diagram, or a block diagram. Although a flowchart can describe the operations as a sequential process, many of the operations can be performed in parallel or concurrently. In addition, the order of the operations can be re-arranged. And a process can have more or fewer operations than are depicted in a figure. A process can correspond to a method, a function, a procedure, a subroutine, a subprogram, etc. When a process corresponds to a function, its termination can correspond to a return of the function to the calling function or the main function.

Systems depicted in some of the figures can be provided in various configurations. In some examples, the systems can be configured as a distributed system where one or more components of the system are distributed across one or more networks in a cloud computing system.

The invention claimed is:

1. A system comprising:
one or more processors; and
one or more memories including program code that is executable by the one or more processors to:
receive heartbeat data generated by a wearable heart-rate sensor worn by a wearer;
execute a noise-reduction process for reducing noise in the heartbeat data, the noise-reduction process involving:
generating a set of filtered heartbeat data by applying a lowpass filter with a cutoff frequency to the heartbeat data;

generating a set of wavelet coefficients by applying a wavelet transform to the set of filtered heartbeat data;

generating a reduced set of wavelet coefficients by applying a threshold to the set of wavelet coefficients, the threshold being configured to reduce noise and motion artifacts represented in the set of wavelet coefficients;

generating an inverse wavelet signal by applying an inverse wavelet transform to the reduced set of wavelet coefficients, wherein each heartbeat in the heartbeat data is represented in the inverse wavelet signal by a P wave, a T wave, and an R wave;

determining instantaneous amplitudes of data points in the inverse wavelet signal, the instantaneous amplitudes being determined using a Hilbert transform;

identifying a set of R-peaks by performing peak detection on the instantaneous amplitudes;

generating a heart rate curve based on the set of R-peaks; and generating a modified heart rate curve by applying a Hampel filter to the heart rate curve;

determining heart rate data based on the modified heart rate curve; and output the heart rate data associated with the wearer.

2. The system of claim 1, wherein the one or more memories further include program code that is executable by the one or more processors to output the heart rate data by displaying the heart rate data on a display device.

3. The system of claim 1, wherein the noise is associated with movement of the wearable heart-rate sensor against a skin of the wearer.

4. The system of claim 1, wherein the one or more memories further include program code that is executable by the one or more processors to:

determine a first parametric power spectral density (PPSD) associated with a first heartbeat signal of the wearer, the first heartbeat signal being collected while the wearer is at rest;

determine a second PPSD associated with a second heartbeat signal of the wearer, the second heartbeat signal being collected while the wearer is in motion; and determine the cutoff frequency for the lowpass filter by comparing the first PPSD to the second PPSD.

5. The system of claim 1, wherein the lowpass filter is a Butterworth filter, and wherein the cutoff frequency for the lowpass filter is between 15 Hertz (Hz) and 25 Hz.

6. The system of claim 1, wherein the one or more memories further include program code that is executable by the one or more processors to determine the instantaneous amplitudes by:

for each data point in the inverse wavelet signal:
determine a transformed amplitude value associated the data point by applying the Hilbert transform to an amplitude value of the data point;
determine an instantaneous amplitude for the data point by computing an absolute value of a sum of (i) the amplitude value of the data point and (ii) the transformed amplitude value associated the data point.

7. The system of claim 1, wherein the threshold is a first threshold, and wherein the noise-reduction process further comprises:

prior to generating the set of filtered heartbeat data, for each observation in the heartbeat data:
computing a z-score for the observation based on an amplitude value of the observation, a mean of a sample of the heartbeat data, and a standard deviation of the sample of the heartbeat data;
determining whether the z-score is greater than or equal to a second threshold; and
based on determining that the z-score is greater than or equal to the second threshold, replacing the amplitude value of the observation with zero in the heartbeat data.

8. The system of claim 1, wherein the threshold is a first threshold, and wherein the Hampel filter is configured to:

for each R-peak in the set of R-peaks:
determine an amplitude of the R-peak;
determine a median value of a data window centered around the R-peak;
determine an absolute value of a difference between the amplitude and the median value;
determine whether the absolute value is greater than or equal to a second threshold; and
based on determining that the absolute value is greater than or equal to the second threshold, replace the amplitude of the R-peak with the median value in the set of R-peaks.

9. The system of claim 1, wherein the wavelet transform is a stationary wavelet transform that is configured to generate scaling coefficients and detail coefficients, and wherein the one or more memories further include program code that is executable by the one or more processors to determine the threshold based on a subset of the detail coefficients.

10. The system of claim 1, wherein the one or more memories further include program code that is executable by the one or more processors to output the heart rate data by transmitting the heart rate data over a network to a remote computing device.

11. A method comprising:

receiving, by one or more processors, heartbeat data generated by a wearable heart-rate sensor worn by a wearer;

executing, by the one or more processors, a noise-reduction process for reducing noise in the heartbeat data, the noise-reduction process involving:

generating a set of filtered heartbeat data by applying a lowpass filter with a cutoff frequency to the heartbeat data;

generating a set of wavelet coefficients by applying a wavelet transform to the set of filtered heartbeat data;

generating a reduced set of wavelet coefficients by applying a threshold to the set of wavelet coefficients, the threshold being configured to reduce noise and motion artifacts represented in the set of wavelet coefficients;

generating an inverse wavelet signal by applying an inverse wavelet transform to the reduced set of wavelet coefficients, wherein each heartbeat in the heartbeat data is represented in the inverse wavelet signal by a P wave, a T wave, and an R wave;

determining instantaneous amplitudes of data points in the inverse wavelet signal, the instantaneous amplitudes being determined using a Hilbert transform;

identifying a set of R-peaks by performing peak detection on the instantaneous amplitudes;

generating a heart rate curve based on the set of R-peaks; and generating a modified heart rate curve by applying a Hampel filter to the heart rate curve;

determining, by the one or more processors, heart rate data based on the modified heart rate curve; and outputting, by the one or more processors, the heart rate data associated with the wearer.

12. The method of claim 11, further comprising outputting the heart rate data by displaying the heart rate data on a display device.

13. The method of claim 11, wherein the noise is associated with movement of the wearable heart-rate sensor against a skin of the wearer.

14. The method of claim 11, further comprising:
determining a first parametric power spectral density (PPSD) associated with a first heartbeat signal of the wearer, the first heartbeat signal being collected while the wearer is at rest;
determining a second PPSD associated with a second heartbeat signal of the wearer, the second heartbeat signal being collected while the wearer is in motion; and
determining the cutoff frequency for the lowpass filter by comparing the first PPSD to the second PPSD.

15. The method of claim 11, wherein the lowpass filter is a Butterworth filter, and wherein the cutoff frequency for the lowpass filter is between 15 Hertz (Hz) and 25 Hz.

16. The method of claim 11, further comprising determining the instantaneous amplitudes by:
for each data point in the inverse wavelet signal:
determining a transformed amplitude value associated the data point by applying the Hilbert transform to an amplitude value of the data point;
determining an instantaneous amplitude for the data point by computing an absolute value of a sum of (i) the amplitude value of the data point and (ii) the transformed amplitude value associated the data point.

17. The method of claim 11, wherein the threshold is a first threshold, and wherein the noise-reduction process further comprises:
prior to generating the set of filtered heartbeat data, for each observation in the heartbeat data:
computing a z-score for the observation based on an amplitude value of the observation, a mean of a sample of the heartbeat data, and a standard deviation of the sample of the heartbeat data;
determining whether the z-score is greater than or equal to a second threshold; and
based on determining that the z-score is greater than or equal to the second threshold, replacing the amplitude value of the observation with zero in the heartbeat data.

18. The method of claim 11, wherein the threshold is a first threshold, and wherein the Hampel filter is configured to:
for each R-peak in the set of R-peaks:
determine an amplitude of the R-peak;
determine a median value of a data window centered around the R-peak;
determine an absolute value of a difference between the amplitude and the median value;
determine whether the absolute value is greater than or equal to a second threshold; and
based on determining that the absolute value is greater than or equal to the second threshold, replace the amplitude of the R-peak with the median value in the set of R-peaks.

19. The method of claim 11, wherein the wavelet transform is a stationary wavelet transform that is configured to generate scaling coefficients and detail coefficients, and further comprising determining the threshold based on a subset of the detail coefficients.

20. The method of claim 11, further comprising outputting the heart rate data by transmitting the heart rate data over a network to a remote computing device.

21. A non-transitory computer-readable medium comprising program code that is executable by one or more processors for causing the one or more processors to:
receive heartbeat data generated by a wearable heart-rate sensor worn by a wearer;
execute a noise-reduction process for reducing noise in the heartbeat data, the noise-reduction process involving:
generating a set of filtered heartbeat data by applying a lowpass filter with a cutoff frequency to the heartbeat data;
generating a set of wavelet coefficients by applying a wavelet transform to the set of filtered heartbeat data;
generating a reduced set of wavelet coefficients by applying a threshold to the set of wavelet coefficients, the threshold being configured to reduce noise and motion artifacts represented in the set of wavelet coefficients;
generating an inverse wavelet signal by applying an inverse wavelet transform to the reduced set of wavelet coefficients, wherein each heartbeat in the heartbeat data is represented in the inverse wavelet signal by a P wave, a T wave, and an R wave;
determining instantaneous amplitudes of data points in the inverse wavelet signal, the instantaneous amplitudes being determined using a Hilbert transform;
identifying a set of R-peaks by performing peak detection on the instantaneous amplitudes;
generating a heart rate curve based on the set of R-peaks; and
generating a modified heart rate curve by applying a Hampel filter to the heart rate curve;
determine heart rate data based on the modified heart rate curve; and
output the heart rate data associated with the wearer.

22. The non-transitory computer-readable medium of claim 21, further comprising program code that is executable by the one or more processors to output the heart rate data by displaying the heart rate data on a display device.

23. The non-transitory computer-readable medium of claim 21, wherein the noise is associated with movement of the wearable heart-rate sensor against a skin of the wearer.

24. The non-transitory computer-readable medium of claim 21, further comprising program code that is executable by the one or more processors to:
determine a first parametric power spectral density (PPSD) associated with a first heartbeat signal of the wearer, the first heartbeat signal being collected while the wearer is at rest;
determine a second PPSD associated with a second heartbeat signal of the wearer, the second heartbeat signal being collected while the wearer is in motion; and
determine the cutoff frequency for the lowpass filter by comparing the first PPSD to the second PPSD.

25. The system non-transitory computer-readable medium of claim 21, wherein the lowpass filter is a Butterworth filter, and wherein the cutoff frequency for the lowpass filter is between 15 Hertz (Hz) and 25 Hz.

26. The non-transitory computer-readable medium of claim 21, further comprising program code that is executable by the one or more processors to determine the instantaneous amplitudes by:

for each data point in the inverse wavelet signal:
   determine a transformed amplitude value associated the data point by applying the Hilbert transform to an amplitude value of the data point;
   determine an instantaneous amplitude for the data point by computing an absolute value of a sum of (i) the amplitude value of the data point and (ii) the transformed amplitude value associated the data point.

27. The non-transitory computer-readable medium of claim 21, wherein the threshold is a first threshold, and wherein the noise-reduction process further comprises:
   prior to generating the set of filtered heartbeat data, for each observation in the heartbeat data:
      computing a z-score for the observation based on an amplitude value of the observation, a mean of a sample of the heartbeat data, and a standard deviation of the sample of the heartbeat data;
      determining whether the z-score is greater than or equal to a second threshold; and
      based on determining that the z-score is greater than or equal to the second threshold, replacing the amplitude value of the observation with zero in the heartbeat data.

28. The non-transitory computer-readable medium of claim 21, wherein the threshold is a first threshold, and wherein the Hampel filter is configured to:
   for each R-peak in the set of R-peaks:
      determine an amplitude of the R-peak;
      determine a median value of a data window centered around the R-peak;
      determine an absolute value of a difference between the amplitude and the median value;
      determine whether the absolute value is greater than or equal to a second threshold; and
      based on determining that the absolute value is greater than or equal to the second threshold, replace the amplitude of the R-peak with the median value in the set of R-peaks.

29. The non-transitory computer-readable medium of claim 21, wherein the wavelet transform is a stationary wavelet transform that is configured to generate scaling coefficients and detail coefficients, and further comprising program code that is executable by the one or more processors to determine the threshold based on a subset of the detail coefficients.

30. The non-transitory computer-readable medium of claim 21, further comprising program code that is executable by the one or more processors to output the heart rate data by transmitting the heart rate data over a network to a remote computing device.

* * * * *

UNITED STATES PATENT AND TRADEMARK OFFICE
CERTIFICATE OF CORRECTION

PATENT NO. : 11,950,933 B1
APPLICATION NO. : 18/527070
DATED : April 9, 2024
INVENTOR(S) : Carol Wagih Sadek et al.

Page 1 of 1

It is certified that error appears in the above-identified patent and that said Letters Patent is hereby corrected as shown below:

In the Specification

In Column 2, Line 12, replace:
"(a Ham pel filter)"
With:
-- (a Hampel filter) --.

In Column 3, Line 15, replace:
"(a Ham pel filter)"
With:
-- (a Hampel filter) --.

Signed and Sealed this
Fourteenth Day of May, 2024

Katherine Kelly Vidal
*Director of the United States Patent and Trademark Office*